(12) United States Patent
Rui et al.

(10) Patent No.: US 8,383,580 B2
(45) Date of Patent: Feb. 26, 2013

(54) METHODS OF ADMINISTERING LIPOCALINS TO TREAT METABOLIC DISORDERS AND CARDIOVASCULAR DISEASES

(75) Inventors: Liangyou Rui, Ann Arbor, MI (US); Yingjiang Zhou, Arlington, MA (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/157,977

(22) Filed: Jun. 10, 2011

(65) Prior Publication Data

US 2012/0010123 A1    Jan. 12, 2012

Related U.S. Application Data

(60) Provisional application No. 61/353,550, filed on Jun. 10, 2010.

(51) Int. Cl.
*A61K 38/00* (2006.01)
*A61K 47/00* (2006.01)
*A61K 38/16* (2006.01)

(52) U.S. Cl. ........................................ 514/1.2; 514/21.3
(58) Field of Classification Search .......................... None
See application file for complete search history.

(56) References Cited

U.S. PATENT DOCUMENTS

| 4,366,241 A | 12/1982 | Tom et al. |
| 4,376,110 A | 3/1983 | David et al. |
| 4,517,288 A | 5/1985 | Giegel et al. |
| 4,837,168 A | 6/1989 | de Jaeger et al. |

FOREIGN PATENT DOCUMENTS

| WO | WO-2008049330 A1 | 5/2008 |
| WO | WO-2009132510 A1 | 11/2009 |
| WO | WO-2010046411 A1 | 4/2010 |

OTHER PUBLICATIONS

Clark et al., The secreted protein discovery initiative (SPDI), a large-scale effort to identify novel human secreted and transmembrane proteins: a bioinformatics assessment. *Genome Res.*, 13 (10):2265-70 (2003).
Strausberg et al., Generation and initial analysis of more than 15,000 full-length human and mouse cDNA sequences. *Proc. Natl. Acad. Sci. U.S.A.*, 99 (26):16899-903 (2002).
Kjeldsen et al., Isolation and primary structure of NGAL, a novel protein associated with human neutrophil gelatinase. *J. Biol Chem.*, 268(14):10425-32 (1993).
International Search Reporting and Written Opinion of the International Searching Authority, PCT/US2011/039986, European Searching Authority, dated Mar. 28, 2012.

*Primary Examiner* — Robert Landsman
(74) *Attorney, Agent, or Firm* — Marshall, Gerstein & Borun LLP

(57) ABSTRACT

A method of treating an LCN13-related condition is provided comprising administering to a patient in need thereof a therapeutically effective amount of a lipocalin or a physiologically active fragment thereof.

7 Claims, 16 Drawing Sheets

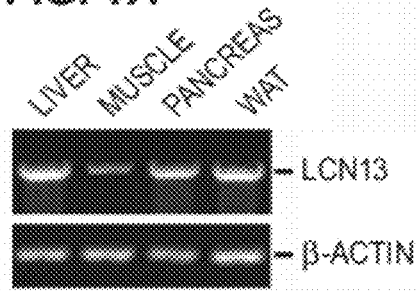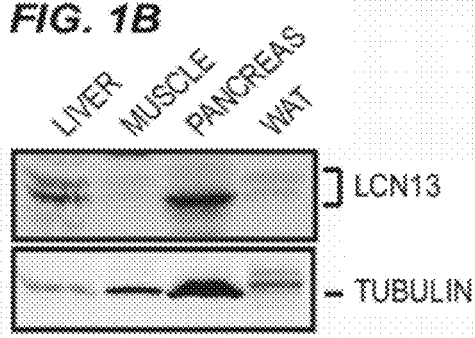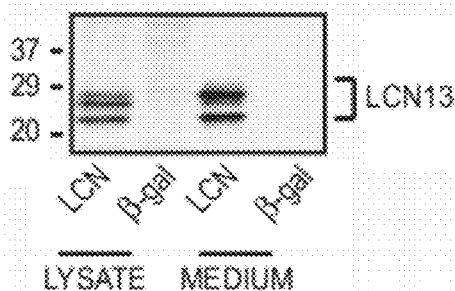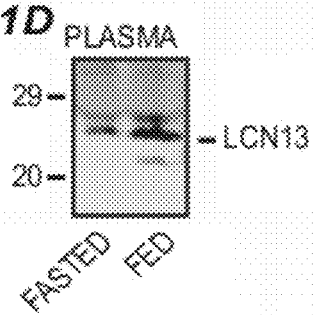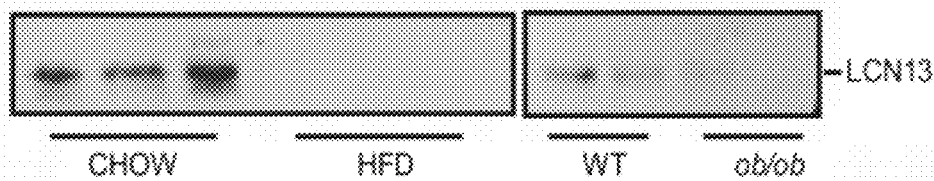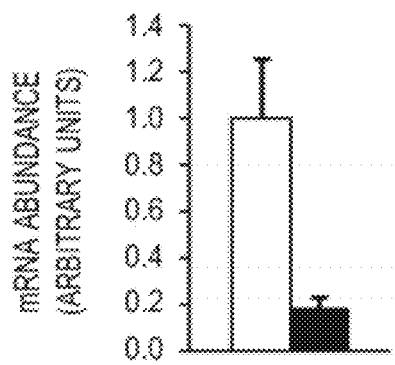

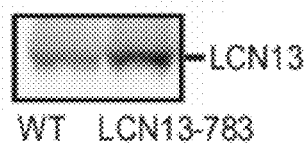
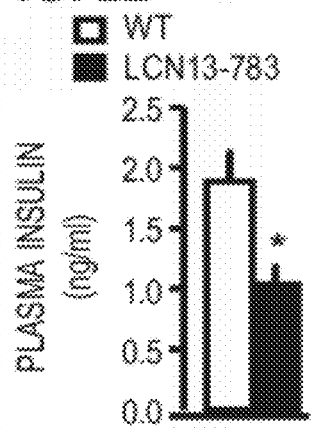
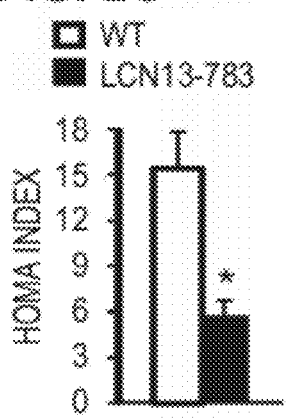
FIG. 2A  FIG. 2B  FIG. 2C
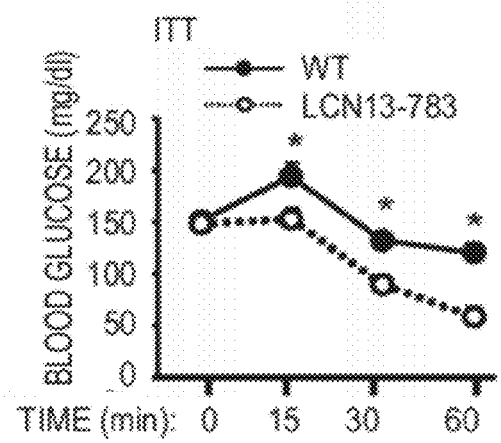
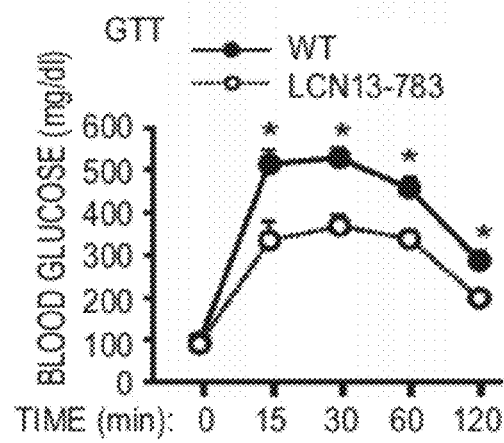
FIG. 2D  FIG. 2E
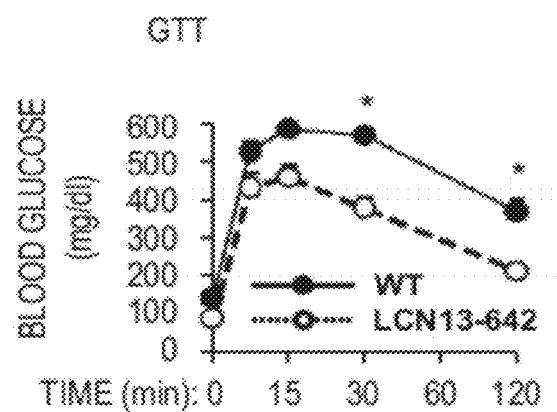
FIG. 2F

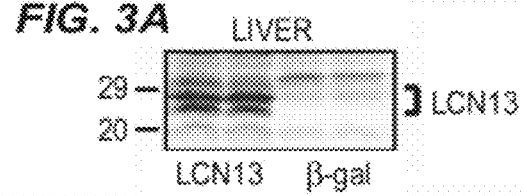
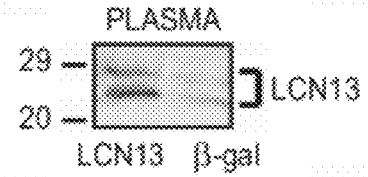
FIG. 3A
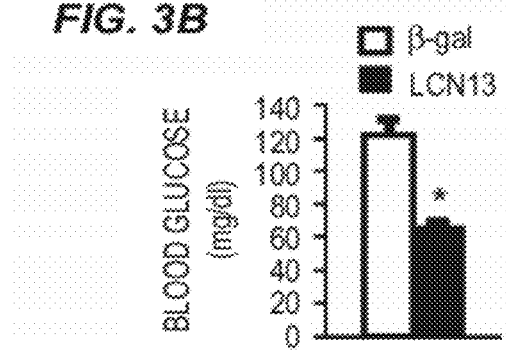
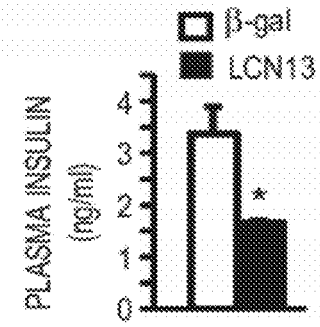
FIG. 3B
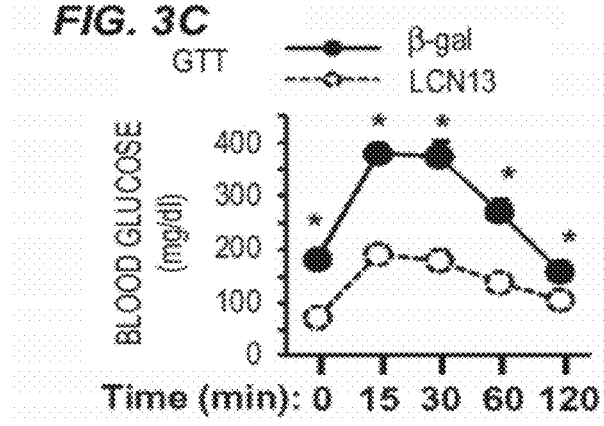
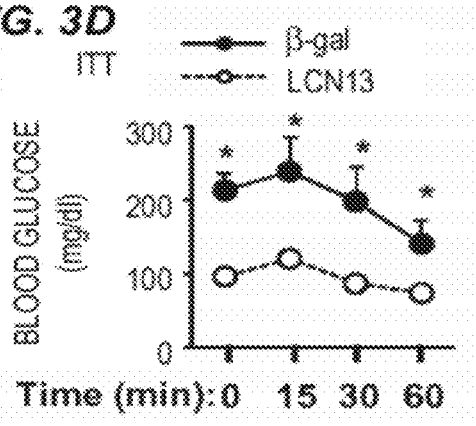
FIG. 3C GTT
FIG. 3D ITT

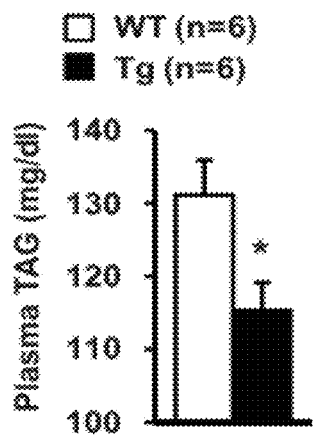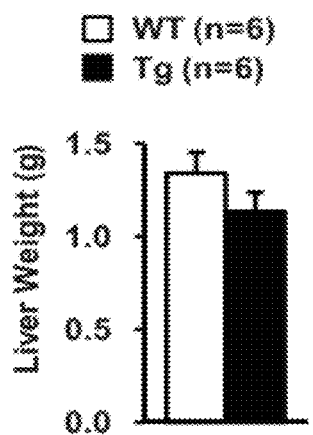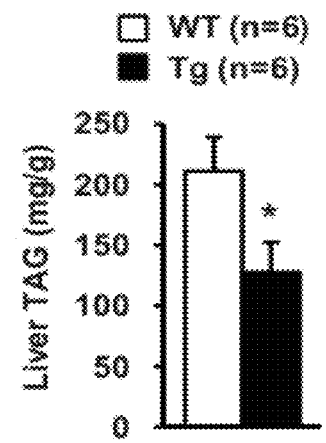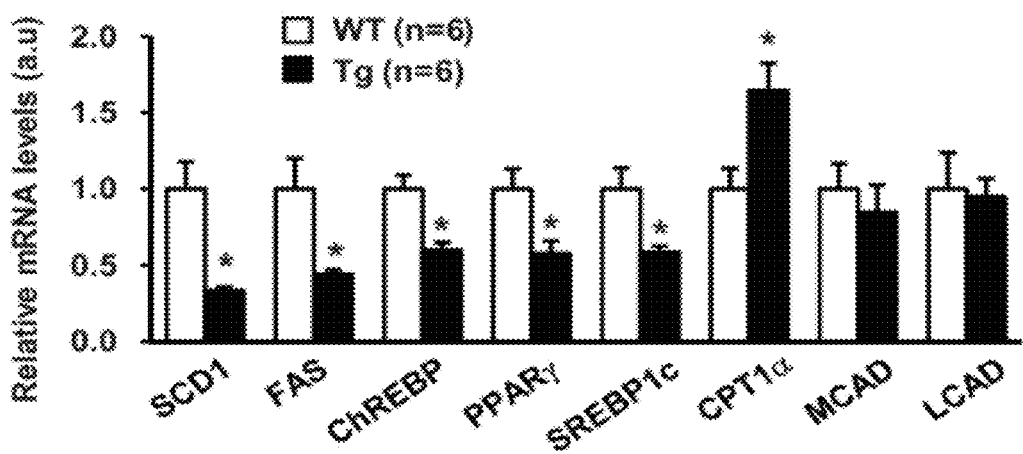

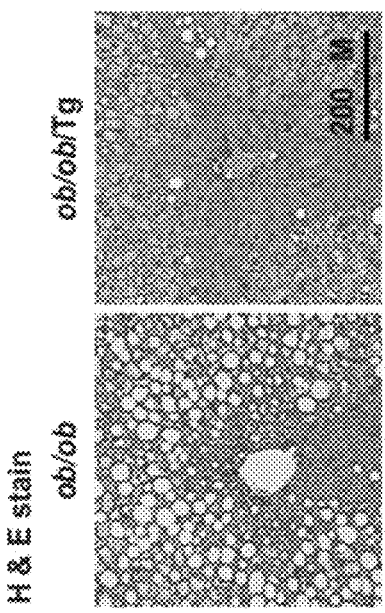
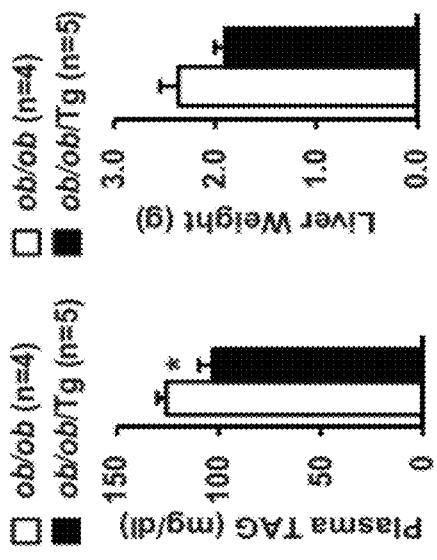
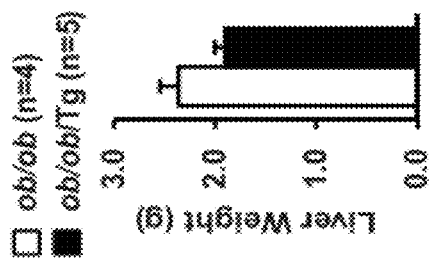
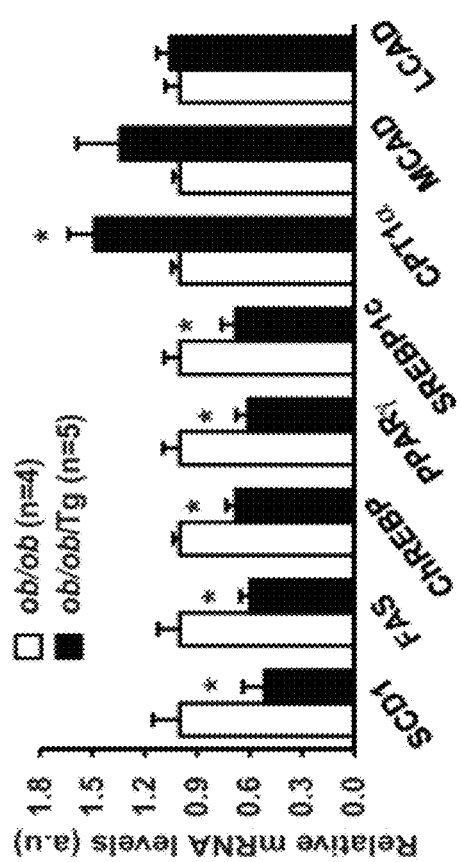
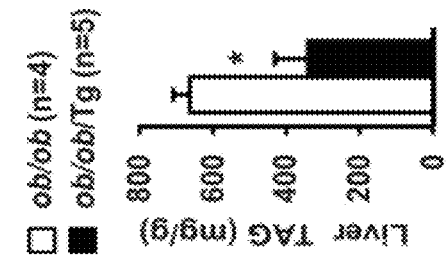

METHODS OF ADMINISTERING LIPOCALINS TO TREAT METABOLIC DISORDERS AND CARDIOVASCULAR DISEASES

CROSS REFERENCE TO RELATED APPLICATIONS

This application claims priority to U.S. Provisional Patent Application No. 61/353,550, filed Jun. 10, 2010, which is hereby incorporated by reference in its entirety.

STATEMENT OF GOVERNMENT INTEREST

This invention was made with government support under Grant Number DK065122 and DK073601 awarded by the National Institutes of Health (NIH). The government has certain rights in the invention.

INCORPORATION BY REFERENCE OF MATERIAL SUBMITTED ELECTRONICALLY

This application contains, as a separate part of the disclosure, a Sequence Listing in computer-readable form (filename: 45409A_SeqListing.txt; created May 24, 2011, 16,592 bytes—ASCII text file) which is incorporated by reference in its entirety.

FIELD OF THE INVENTION

The invention relates to methods of treating lipocalin 13-related conditions such as metabolic disorders and cardiovascular diseases.

BACKGROUND OF THE INVENTION

Insulin controls glucose homeostasis by both suppressing hepatic glucose production and stimulating glucose uptake into skeletal muscle and adipose tissue. Impaired insulin action (insulin resistance) contributes to multiple metabolic disorders, including type 2 diabetes, dyslipidemia and cardiovascular diseases. Insulin resistance is not only a hallmark but also a determinant of type 2 diabetes.

Obesity is the primary risk factor for insulin resistance. Multiple factors contribute to insulin resistance. Abnormal lipid accumulation impairs insulin action in skeletal muscle and livers, thereby contributing to systemic insulin resistance in obesity. Obesity is associated with chronic, low grade inflammation that also contributes to insulin resistance. Additionally, adipocytes secrete a variety of polypeptides, collectively called adipokines, which regulate insulin sensitivity. Many proinflammatory cytokines and adipokines have been documented to regulate insulin sensitivity.

Hepatic lipid levels are determined by several physiological processes, including lipogenesis, fatty acid β oxidation, lipid uptake, and very low density lipoprotein (VLDL) secretion. These processes are tightly controlled by metabolites and metabolic hormones, and aberrant regulation results in hepatic steatosis, leading to nonalcoholic fatty liver disease (NAFLD), nonalcoholic steatohepatitis (NASH), cirrhosis, and liver failure.

The liver is the key organ for the maintenance of lipid homeostasis. During the fed state, glucose is taken up by hepatocytes and converted to fatty acids and triacylglycerols that are exported via VLDL to extrahepatic tissues. During the fasted state, fatty acids are oxidized to generate ATP and ketone bodies. Ketone bodies, a metabolic fuel, are exported to extrahepatic tissues. Hepatic lipogenesis and fatty acid β oxidation are precisely regulated by metabolic hormones, including insulin and glucagon.

A major therapeutic goal in treating type 2 diabetes is to improve insulin sensitivity. It is extremely important to identify molecules that sensitize insulin action. Moreover, obesity is an important risk factor for NAFLD. Thus, there exists in the art a need for improved methods of treating and preventing metabolic disorders and cardiovascular disease.

SUMMARY OF THE INVENTION

In one aspect of the disclosure, there is provided a method of treating a lipocalin 13 (LCN13)-related condition comprising administering to a patient in need thereof a therapeutically effective amount of a lipocalin or a physiologically active fragment thereof.

In various aspects, the lipocalin is a protein with a sequence at least 45% similar to SEQ ID NO: 1, at least 50% similar to SEQ ID NO: 1, at least 55% similar to SEQ ID NO: 1, at least 50% similar to SEQ ID NO: 1, at least 60% similar to SEQ ID NO: 1, at least 65% similar to SEQ ID NO: 1, at least 70% similar to SEQ ID NO: 1, at least 75% similar to SEQ ID NO: 1, at least 80% similar to SEQ ID NO: 1, at least 85% similar to SEQ ID NO: 1, at least 90% similar to SEQ ID NO: 1, is at least 95% similar to SEQ ID NO: 1, at least 96% similar to SEQ ID NO: 1, at least 97% similar to SEQ ID NO: 1, at least 98% similar to SEQ ID NO: 1, or at least 99% similar to SEQ ID NO: 1.

In other aspects, the lipocalin is a protein with a sequence at least 45% identical to SEQ ID NO: 1, at least 50% identical to SEQ ID NO: 1, at least 55% identical to SEQ ID NO: 1, at least 50% identical to SEQ ID NO: 1, at least 60% identical to SEQ ID NO: 1, at least 65% identical to SEQ ID NO: 1, at least 70% identical to SEQ ID NO: 1, at least 75% identical to SEQ ID NO: 1, at least 80% identical to SEQ ID NO: 1, at least 85% identical to SEQ ID NO: 1, at least 90% identical to SEQ ID NO: 1, at least 95% identical to SEQ ID NO: 1, at least 96% identical to SEQ ID NO: 1, at least 97% identical to SEQ ID NO: 1, at least 98% identical to SEQ ID NO: 1, or at least 99% identical to SEQ ID NO: 1.

In another aspect of the method, the lipocalin has the amino acid sequence set out in SEQ ID No: 1.

In another aspect of the method, the lipocalin is selected from the group consisting of LCN1 (SEQ ID NO: 30), LCN3 (SEQ ID NO: 31), LCN4 (SEQ ID NO: 32), LCN14 (SEQ ID NO: 33), OBP2B (SEQ ID NO: 34), and OBP2A (SEQ ID NO: 35). In some embodiments, the lipocalin is a protein with a sequence at least 45% similar to SEQ ID NOs: 30, 31, 32, 33, 34, or 35, at least 50% similar to SEQ ID NOs: 30, 31, 32, 33, 34, or 35, at least 55% similar to SEQ ID NOs: 30, 31, 32, 33, 34, or 35, at least 50% similar to SEQ ID NOs: 30, 31, 32, 33, 34, or 35, at least 60% similar to SEQ ID NOs: 30, 31, 32, 33, 34, or 35, at least 65% similar to SEQ ID NOs: 30, 31, 32, 33, 34, or 35, at least 70% similar to SEQ ID NOs: 30, 31, 32, 33, 34, or 35, at least 75% similar to SEQ ID NOs: 30, 31, 32, 33, 34, or 35, at least 80% similar to SEQ ID NOs: 30, 31, 32, 33, 34, or 35, at least 85% similar to SEQ ID NOs: 30, 31, 32, 33, 34, or 35, at least 90% similar to SEQ ID NOs: 30, 31, 32, 33, 34, or 35, is at least 95% similar to SEQ ID NOs: 30, 31, 32, 33, 34, or 35, at least 96% similar to SEQ ID NOs: 30, 31, 32, 33, 34, or 35, at least 97% similar to SEQ ID NOs: 30, 31, 32, 33, 34, or 35, at least 98% similar to SEQ ID NOs: 30, 31, 32, 33, 34, or 35, or at least 99% similar to SEQ ID NOs: 30, 31, 32, 33, 34, or 35. In some embodiments, the lipocalin is a protein with a sequence at least 45% identical to SEQ ID NOs: 30, 31, 32, 33, 34, or 35, at least 50% identical to SEQ ID NOs: 30, 31, 32, 33, 34, or 35, at least 55% identical to SEQ ID NOs: 30, 31, 32, 33, 34, or 35, at least 50% identical to SEQ ID NOs: 30, 31, 32, 33, 34, or 35, at least 60% identical to SEQ ID NOs: 30, 31, 32, 33, 34, or 35, at least 65% identical to SEQ ID NOs: 30, 31, 32, 33, 34, or 35, at least 70% identical to SEQ ID NOs: 30, 31, 32, 33, 34, or 35, at least 75% identical to SEQ ID NOs: 30, 31, 32, 33, 34, or 35, at least 80% identical to SEQ ID NOs: 30, 31, 32, 33, 34, or 35, at least 85% identical to SEQ ID NOs: 30, 31, 32, 33, 34, or 35, at least 90% identical to SEQ ID NOs: 30, 31, 32, 33, 34, or 35, at least 95% identical to SEQ ID NOs: 30, 31, 32, 33, 34, or 35, at least 96% identical to SEQ ID NOs: 30, 31, 32, 33, 34, or 35, at least 97% identical to SEQ ID NOs: 30, 31, 32, 33, 34, or 35, at least 98% identical to SEQ ID NOs: 30, 31, 32, 33, 34, or 35, or at least 99% identical to SEQ ID NOs: 30, 31, 32, 33, 34, or 35.

In another aspect of the method, the LCN13 fragment comprises residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1. In some embodiments, the LCN13 fragment is a protein with a sequence at least 45% similar to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 50% similar to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 55% similar to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 50% similar to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 60% similar to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 65% similar to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 70% similar to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 75% similar to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 80% similar to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 85% similar to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 90% similar to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, is at least 95% similar to SEQ ID NO: 1, at least 96% similar to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 97% similar to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 98% similar to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, or at least 99% similar to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1. In some embodiments, the LCN13 fragment is a protein with a sequence at least 45% identical to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 50% identical to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 55% identical to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 50% identical to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 60% identical to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 65% identical to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 70% identical to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 75% identical to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 80% identical to residues 19 through 176 in SEQ ID No. 1, residues 32 through 135 in SEQ ID No. 1, residues 54 through 124 in SEQ ID No.

1, residues 25 through 176 in SEQ ID No. 1, residues 25 through 166 in SEQ ID No. 1, or residues 19 through 166 in SEQ ID No. 1, at least 85% identical to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 90% identical to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 95% identical to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 96% identical to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 97% identical to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, at least 98% identical to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1, or at least 99% identical to residues 19 through 176 in SEQ ID No. 1, residues 32 through 135 in SEQ ID No. 1, residues 54 through 124 in SEQ ID No. 1, residues 25 through 176 in SEQ ID No. 1, residues 25 through 166 in SEQ ID No. 1, or residues 19 through 166 in SEQ ID No. 1.

Methods provided contemplate treatment of an LCN13-related condition selected from the group consisting of a metabolic disorder and a cardiovascular disease.

In various aspects of the method, the metabolic disorder is selected from the group consisting of type 1 diabetes, type 2 diabetes, hyperglycemia, hyperinsulinemia, insulin resistance, and obesity. In another aspect, the lipocalin is co-administered with a therapeutically effective amount of insulin.

In methods for the treatment of cardiovascular disease, the cardiovascular disease is selected from the group consisting of hypercholesterolemia, non-familial hypercholesterolemia, familial hypercholesterolemia, heterozygous familial hypercholesterolemia, homozygous familial hypercholesterolemia, mixed dyslipidemia, atherosclerosis, a risk of developing atherosclerosis, coronary heart disease, a history of coronary heart disease, early onset coronary heart disease, one or more risk factors for coronary heart disease, dyslipidemia, hypertriglyceridemia, hyperlipidemia, hyperfattyacidemia, hepatic steatosis, non-alcoholic steatohepatitis (NASH), cirrhosis, liver failure, and non-alcoholic fatty liver disease (NAFLD). In another aspect, the lipocalin is co-administered in a combination therapy regimen.

Also provided herein is a method of improving insulin sensitivity and glucose metabolism in an individual comprising administering to a patient in need thereof a therapeutically effective amount of a lipocalin. In some embodiments, insulin sensitivity is improved in adipocytes. In some embodiments, insulin sensitivity is improved in muscle cells. In some embodiments, insulin sensitivity is improved in liver cells.

Also provided herein is a method of suppressing hepatic glucose production in an individual comprising administering to a patient in need thereof a therapeutically effective amount of a lipocalin.

Also provided herein is a method of suppressing hepatic lipogenesis in primary hepatocytes in an individual comprising administering to a patient in need thereof a therapeutically effective amount of a lipocalin.

Also provided herein is a method of promoting fatty acid β oxidation in primary hepatocytes in an individual comprising administering to a patient in need thereof a therapeutically effective amount of a lipocalin.

Also provided herein is a method of treating hepatosteatosis in an individual comprising administering to a patient in need thereof a therapeutically effective amount of a lipocalin. In some embodiments, the hepatosteatosis is diet-induced hepatosteatosis.

Also provided herein is a method of reducing lipid levels in an individual comprising administering to a patient in need thereof a therapeutically effective amount of a lipocalin to reduce a lipid level. In various aspects of this method, the lipid is selected from the group consisting of LDL-C, ApoB, VLDL-C, IDL-C, non-HDL-C, Lp(a), serum triglyceride (i.e., triacylgycerol), liver triglyceride, Ox-LDL-C, small LDL particles, small VLDL, phospholipids, and oxidized phospholipids. In certain aspects, the lipocalin is co-administered with a therapeutically effect amount of a lipid-lowering agent, and in various embodiments, the lipid-lowering agent is selected from the group consisting of atorvastatin, simvastatin, rosuvastatin, fluvastatin, lovastatin, pravastatin, and ezetimibe.

Also provided herein is a method for diagnosing an LCN13-related condition in a test individual comprising the step of determining a lipocalin level in a sample from the test individual, wherein a lipocalin level that is reduced in the test individual compared to a lipocalin level in a normal individual is suggestive of an LCN-related condition and wherein the normal individual is known not to suffer from an LCN13-related condition. In some embodiments, the lipocalin is selected from the group consisting of LCN13, LCN1, LCN3, LCN4, LCN14, OBP2B, and OBP2A.

Also provided herein is a method for diagnosing an LCN13-related condition in an individual comprising the step of detecting lipocalin levels in a sample from the individual, wherein a lipocalin level that is reduced compared to a prior lipocalin level in the same individual is suggestive of an LCN13-related condition. In some embodiments, the lipocalin is selected from the group consisting of LCN13, LCN1, LCN3, LCN4, LCN14, OBP2B, and OBP2A.

Also provided herein is a method for determining susceptibility to an LCN13-related condition in a test individual comprising the step of determining a lipocalin level in a sample from the test individual, wherein a reduced lipocalin level in the test individual compared to lipocalin level in a sample from a normal individual indicates susceptibility to an LCN13-related condition, and wherein the normal individual is known not to suffer from an LCN13-related condition. In some embodiments, the lipocalin is selected from the group consisting of LCN13, LCN1, LCN3, LCN4, LCN14, OBP2B, and OBP2A.

Also provided herein is a method for determining susceptibility to an LCN13-related condition in an individual comprising the step of detecting a lipocalin level in a sample from the individual, wherein a lipocalin level that is reduced in the individual compared to prior lipocalin level in the same individual is suggestive of susceptibility to an LCN13-related condition. In some embodiments, the lipocalin is selected from the group consisting of LCN13, LCN1, LCN3, LCN4, LCN14, OBP2B, and OBP2A.

Also provided herein is a method for determining the progression of an LCN13-related condition in an individual comprising the step of determining lipocalin levels in samples from the individual over time, wherein a decrease in lipocalin level over time is suggestive of progression of the LCN13-related condition.

Also provided herein is a method for monitoring the effectiveness of an LCN13-related condition treatment from an individual comprising the step of determining lipocalin levels in samples from the individual over time, wherein an increase in lipocalin level over time is suggestive of effective treatment. In some embodiments, the lipocalin is selected from the group consisting of LCN13, LCN1, LCN3, LCN4, LCN14, OBP2B, and OBP2A.

In various aspects of the methods, a lipocalin level is a measure of serum protein concentration. In another aspect, a lipocalin level is a measure of lipocalin activity. In another aspect, the lipocalin level is a measure of transcription of a lipocalin-encoding gene. In another aspect, the lipocalin activity is specific binding activity. In some embodiments, the lipocalin is selected from the group consisting of LCN13, LCN1, LCN3, LCN4, LCN14, OBP2B, and OBP2A.

Other features and advantages of the present disclosure will become apparent from the following detailed description. It should be understood, however, that the detailed description and the specific examples, while indicating preferred embodiments of the disclosure, are given by way of illustration only, because various changes and modifications within the spirit and scope of the disclosure will become apparent to those skilled in the art from this detailed description.

BRIEF DESCRIPTION OF THE DRAWINGS

FIGS. 1A-1F illustrate experimental results indicating that obesity is associated with reduced LCN13 expression and secretion. (A) Total RNA was extracted from the liver, skeletal muscle, pancreas and white adipose tissue (WAT) of male mice (8 weeks) and used to detect the expression of LCN13 and β-actin by RT-PCR. (B) Tissue extracts were prepared from wild type males (16 weeks) and immunoblotted with antiLCN13 (αLCN13) or αtubulin antibodies. (C) FAO cells were infected with β-gal or LCN13 adenoviruses. Culture medium and cell extracts were prepared 48 h after infection and immunoblotted with αLCN13. (D) Plasma was collected from fasted (16 h) or randomly-fed males (12 weeks) and immunoblotted with αLCN13. (E) Left panel: plasma was prepared from males (8 weeks) fed normal chow diet or a high-fat diet (HFD) for 6 weeks, immunoprecipitated with αLCN13, and immunoblotted with αLCN13. Right panel: plasma was prepared from WT and ob/ob males (12 weeks), immunoprecipitated with αLCN13, and immunoblotted with αLCN13. Each lane represents an individual mouse. (F) C56BL males (8 weeks) were fed a normal chow (n=7) or HFD (n=8) for 8 weeks. Mice were fasted overnight. Total RNAs were extracted from the liver and used to measure the abundance of LCN13 mRNA by qRT-PCR. LCN13 expression was normalized to β-actin expression.

FIGS. 2A-2F illustrate experimental results indicating that transgenic overexpression of LCN13 protects against diet-induced hyperglycemia, glucose intolerance, and insulin resistance. (A) Plasma was prepared from LCN13 transgenic (LCN13-783) and wild type (WT) male littermates (8 weeks), immunoprecipitated with αLCN13, and immunoblotted with αLCN13. (B-E) LCN13-783 and WT male littermates (7 weeks) were fed HFD. (B-C) Fasting (16 h) plasma insulin (B) and HOMA index (C) in WT n=10) and LCN13-783 (n=5) mice fed HFD for 11 weeks. (D) Insulin tolerance tests (ITT) were performed on WT (n=10) and LCN13-783 (n=8) mice fed HFD for 12 weeks (insulin: 1 U/kg body weight). (E) Glucose tolerance tests (GTT) were performed on WT (n=10) and LCN13-783 (n=8) mice fed HFD for 12 weeks (D-glucose: 2 g/kg body weight). (F) GTT (2 g/kg body weight) in LCN13-642 (n=8) and W (n=10) male littermates fed a HFD for 10 weeks. Error bars represent SEM. *P<0.05.

FIGS. 3A-3D illustrate experimental results indicating that adenovirus-mediated overexpression of LCN13 ameliorates hyperglycemia and glucose intolerance in genetic type 2 diabetes. db/db males (9 weeks) were infected with (β-gal or LCN13 adenoviruses via tail vein injection. (A) Plasma and liver extracts were prepared 16 days after infection and immunoblotted with αLCN13. (B) Fasting (16 hours) blood glucose and plasma insulin in mice 6 days after β-gal (n=8) or LCN13 (n=8) adenoviral infection. (C) GTT was performed on mice 10 days after β-gal (n=8) or LCN13 (n=8) adenoviral infection (D-glucose: 0.8 g/kg body weight). (D) ITT was performed on mice 14 days after β-gal (n=8) or LCN13 (n=8) adenoviral infection (insulin: 2 U/kg body weight). Error bars represent SEM. *P<0.05.

FIGS. 12A-12D illustrate experimental results indicating that LCN13 transgenic mice resist diet-induced hepatosteatosis. LCN13 transgenic (Tg) and wild type (WT) male littermates (7 weeks) were fed an HFD. Mice were fasted for 16 hours and euthanized. (A) Plasma triacylglycerol (TAG) levels at 18 weeks of age. (B) Liver weights at 20 weeks of age. (C) Liver TAG levels at 20 weeks of age (normalized to liver weights). (D) The expression of the indicated genes was measured by qRT-PCR and normalized to 36B4 expression. Error bars represent SEM. *P<0.05.

FIGS. 14A-14E illustrate experimental results indicating that transgenic expression of LCN13 ameliorates hepatosteatosis in ob/ob mice. (A) Plasma TAG levels (at 11 weeks of age). (B) Liver weights at 13 weeks of age. (C) Liver sections were stained with hematoxylin & eosin. (D) Liver TAG levels were measured at 13 weeks of age and normalized to liver weights. (E) The expression of the indicated genes was measured by qRT-PCR and normalized to 36B4 expression. Error bars represent SEM. *P<0.05.

DETAILED DESCRIPTION

Definitions

Figure 4A:
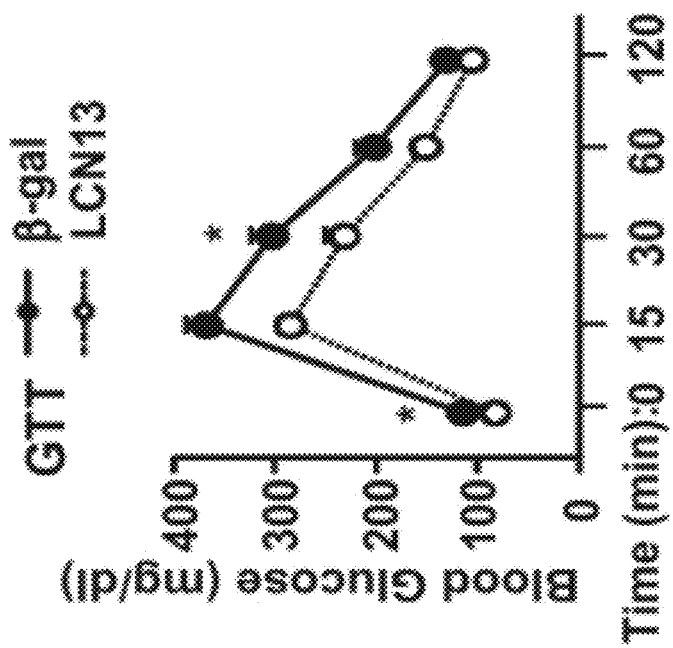
FIGS. 4A-4C illustrate experimental results indicating that liver overexpression of LCN13 improves diet-induced insulin sensitivity and glucose intolerance. (A-C) Male mice (7 weeks) were fed HFD for 10 weeks and infected with β-gal (n=8) or LCN13 (n=8) adenoviruses. (A) Fasting (16 h) blood glucose in mice 6 days after viral infection. (B) ITT was performed on mice 8 days after viral infection (insulin: 1 U/kg body weight). (C) GTT was performed on mice 10 days after infection (D-glucose: 2 g/kg body weight).

As used herein, the term "LCN13" (SEQ ID NO: 1) refers to the protein encoded by the LCN13 gene that was initially identified by its genomic location in the epididymal lipocalin cluster in mouse chromosome 2 (Suzuki et al., *Gene,* 339, 49-59 (2004). Based on its predicted amino acid sequences, LCN13 belongs to the lipocalin super-family. The LCN13 gene contains 7 exons and is predicted to encode 176 amino acids with a putative N-terminal signal peptide (1-18 amino acids) (Accession number: AAR11375; deposited in 2004). Numbering for the fragments is in reference to the complete 176 amino acid protein in Accession number AAR11375.

As used herein, the term "treating" or "treatment" refers to administering a lipocalin, e.g., LCN13, LCN1, LCN3, LCN4, LCN14, OBP2B, or OBP2A to a patient in need thereof as described herein to effect an alteration or improvement of the disease or condition. Treatment in certain aspects, requires administration of a single dose or multiple doses at regular intervals to alter the course of the condition.

As used herein, "administering" means providing a pharmaceutical agent to an animal, including a human patient, and includes, but is not limited to administering by a medical professional and self-administering.

As used herein, the term "co-administration" refers to administration of two or more pharmaceutical agents to an animal, including a human patient. In certain aspects, the pharmaceutical agents are in a single pharmaceutical composition or in separate pharmaceutical compositions. Co-administration includes administering each pharmaceutical agent through the same or different routes of administration. Co-administration also encompasses administration in parallel or sequentially.

As used herein, the term "therapeutically effective amount" refers to an amount of a pharmaceutical agent that provides a therapeutic benefit to an animal, including a human patient.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990).

As used herein, the term "metabolic disorder" refers to a condition characterized by an alteration or disturbance in metabolic function. "Metabolic" and "metabolism" are terms well know in the art and generally include the whole range of biochemical processes that occur within a living organism.

"Insulin resistance" as used herein describes a condition in which physiological amounts of insulin are inadequate to produce a normal insulin response from cells or tissues.

"Insulin sensitizer" as used herein is a compound or drug that increases cell- or tissue-sensitivity to insulin resulting in greater levels of glucose uptake for a given subsaturating concentration of insulin.

As used herein, the term "reduced coronary heart disease risk" refers to a reduction in the likelihood that a individual will develop coronary heart disease. In certain embodiments, a reduction in coronary heart disease risk is measured by an improvement in one or more CHD risk factors, for example, a decrease in LDL-C levels.

The term "similar" or "similarity" refers to substitutions of amino acids with amino acids having similar properties, e.g. size, charge, hydrophobicity, hydrophilicity, and/or aromaticity, and includes exchanges as indicated below (see e.g., Korf et al., BLAST, Chapter 4: Sequence Similarity, O'Reilly Media, Inc. (2003)). Thus, "% similarity" refers to the percentage of residues that are both identical and similar between compared proteins:

| Original | Exemplary |
|---|---|
| Ala (A) | val; leu; ile |
| Arg (R) | lys; gln; asn |
| Asn (N) | gln; his; asp, lys; gln |
| Asp (D) | glu; asn |
| Cys (C) | ser; ala |
| Gln (Q) | asn; glu |
| Glu (E) | asp; gln |
| Gly (G) | ala |
| His (H) | asn; gln; lys; arg |
| Ile (I) | leu; val; met; ala; phe; norleucine |
| Leu (L) | norleucine; ile; val; met; ala; phe |
| Lys (K) | arg; gln; asn |
| Met (M) | leu; phe; ile |
| Phe (F) | leu; val; ile; ala; tyr |
| Pro (P) | ala |
| Ser (S) | thr |
| Thr (T) | ser |
| Trp (W) | tyr; phe |
| Tyr (Y) | trp; phe; thr; ser |
| Val (V) | ile; leu; met; phe; ala; norleucine |

Amino acid residues which share common side-chain properties are grouped as follows.
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Lipocalins

Lipocalins are small secretory proteins involved in a variety of biological processes, including chemical communication, cell proliferation and differentiation, and metabolism. The diverse lipocalin super-family members share a relatively low level of homology in amino acid sequences; however, their tertiary structures are highly conserved, containing a characteristic β-barrel at the center. Lipocalins bind via this central cavity to small lipophilic molecules, including fatty acids, retinol, steroids, odorants, and pheromones. Thus, lipocalins are predicted to act as carriers to regulate the transportation, stability, release, and activity of these small bioactive molecules. Additionally, several lipocalins may bind to their cognate receptors and directly stimulate cellular responses.

Several lipocalin family members appear to be involved in the regulation of insulin action. For instance, the levels of retinol-binding protein (RBP)4, a lipocalin family member, are increased in obesity. RBP4 promotes insulin resistance. Lipocalin 2 also induces insulin resistance, and major urinary protein 1 (MUP1), a lipocalin family membrane primarily expressed in hepatocytes, improves insulin sensitivity and glucose metabolism in mice. MUP1 overexpression markedly improves hyperglycemia and glucose intolerance in mice with type 2 diabetes.

In a search for additional lipocalins that may regulate insulin sensitivity and glucose metabolism, gene expression patterns in the livers of db/db mice were profiled using Affymetrix GeneChip analysis. As shown herein, lipocalin-13 (LCN13) was identified as a potential candidate. The LCN13 gene was initially identified by its genomic location in the epididymal lipocalin cluster in mouse chromosome 2. Based on its predicted amino acid sequences, LCN13 belongs to the lipocalin super-family. The LCN13 gene contains 7 exons and is predicted to encode 176 amino acids with a putative N-terminal signal peptide (1-18 amino acids). Prior to the instant disclosure, LCN13 protein had not been demonstrated in cells or animals, and an LCN13 function was unknown.

LCN13 appears to target multiple cell types, including adipocytes and hepatocytes. In the absence of insulin, LCN13 increases basal glucose uptake in adipocytes (after 6 h treatments) and suppresses glucose production in hepatocytes, suggesting that LCN13 is able to regulate glucose metabolism. Two isoforms of LCN13 were detected in both cells and the bloodstream and methods provided herein contemplate use of either isoform or both isoforms. LCN13 shares a high similarity in amino acids with several other lipocalin family members, including LCN1 (58%), LCN3 (58%), LCN4 (54%) LCN14 (71%), odorant binding protein (OBP) 2B (67%), and OBP2A (60%).

LCN13 protein is secreted into the bloodstream by multiple cell types, and circulating LCN13 is markedly reduced in obese animals. Restoration of circulating LCN13 levels improves hyperglycemia, hyperinsulinemia and glucose intolerance in type 2 diabetes.

Methods provided thus include those wherein the lipocalin to be administered is at least 45% similar, at least 50% similar, at least 55% similar, at least 60% similar, at least 65% similar, at least 70% similar, at least 75% similar, at least 80% similar, at least 85% similar, at least 90% similar, at least 95% similar, at least 96% similar, at least 97% similar, at least 98% similar, or at least 99% similar to SEQ ID NO: 1. Similarly, methods also include those wherein the lipocalin to be administered is at least 45% identical, at least 50% identical, at least 55% identical, at least 60% identical, at least 65% identical, at least 70% identical, at least 75% identical, at least 80% identical, at least 85% identical, at least 90% identical, at least 95% identical, at least 96% identical, at least 97% identical, at least 98% identical, or at least 99% identical to SEQ ID NO: 1.

More specific methods provided include those wherein the lipocalin is a protein in the lipocalin family of proteins, including but not limited to LCN13 (SEQ ID NO: 1), LCN1 (SEQ ID NO: 30) (Accession number: AAH65721; deposited in 2006) (Strausberg et al., Proc. Natl. Acad. Sci. U.S.A. 99 (26), 16899-16903 (2002)), LCN3 (SEQ ID NO: 31) (Accession number: AAI16817; deposited in 2006) (Strausberg et al.), LCN4 (SEQ ID NO: 32) (Accession number: AAI14545; deposited in 2006) (Strausberg et al.), LCN14 (SEQ ID NO: 33), OBP2B (SEQ ID NO: 34) (Accession number: AAQ89340; deposited in 2003) (Clark et al., Genome Res. 13 (10), 2265-2270 (2003)), and OBP2A (SEQ ID NO: 35) (Accession number: CAI14043).

Also envisioned in this disclosure are methods comprising administration of one or more physiologically active fragments of a lipocalin to treat an LCN13-related condition. LCN13 fragments include, but are not limited to, an LCN13 fragment that lacks the first 18 residues (i.e., the signal sequence) of SEQ ID NO: 1, a fragment that comprises or consists of amino acid residues 25 through 176, residues 25 through 166, residues 32 through 135, residues 54 through 124, or residues 19 through 166 of SEQ ID NO: 1. A person of skill in the art can readily screen for active fragments by screening for activity in a relevant biological assay. In various embodiments, an LCN13 fragment comprises or consists of amino acid residues x to y, wherein x is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 and y is 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, or 176.

A lipocalin for use in a method provided is derived from any method known in the art. For example, the lipocalin (e.g., LCN13, LCN1, LCN3, LCN4, LCN14, OBP2B, and OBP2A) in one aspect is derived from cells that express the endogenous lipocalin. Alternatively, the source of the lipocalin or fragment thereof is derived from cells that are transformed with a nucleic acid vector that encodes a lipocalin or a precursor thereof, and are in various aspects mammalian cells, bacterial cells, yeast cells, insect cells, whole organisms, or other cells that are a useful source recombinant protein.

Thus isolated DNA and/or recombinant vectors that encode a recombinant lipocalin protein and control sequences that direct protein expression in bacterial, mammalian or insect cells are provided. In some cases it is desirable that the recombinant lipocalin coding sequence be fused with an additional amino acid sequence that can, without limitation, facilitate recombinant protein purification. For example, in one aspect, expressed lipocalin protein is expressed as a fusion protein that includes one or more histidine tags, glutathione S-transferase (GST) sequences, maltose binding protein (MBP) sequences, Flag sequences and/or myc tagged RGT sequences. These additional sequences which aid in purification of the recombinant protein are optionally removed by protease cleavage.

LCN13-Related Conditions

Methods provided are utilized for the treatment of any condition that can be alleviated by administration of a lipocalin protein or biologically active fragment. In some aspects of methods provided, the LCN13-related condition is a metabolic disorder. Exemplary metabolic disorders considered LCN13-related conditions include, but are not limited to, type 1 diabetes, type 2 diabetes, hyperglycemia, hyperinsulinemia, insulin resistance, and obesity. In other aspects, the LCN13-related condition is a cardiovascular disease. Exemplary cardiovascular diseases considered LCN13-related conditions include, but are not limited to, hypercholesterolemia, non-familial hypercholesterolemia, familial hypercholesterolemia, heterozygous familial hypercholesterolemia, homozygous familial hypercholesterolemia, mixed dyslipidemia, atherosclerosis, a risk of developing atherosclerosis, coronary heart disease, a history of coronary heart disease, early onset coronary heart disease, one or more risk factors for coronary heart disease, dyslipidemia, hypertriglyceridemia, hyperlipidemia, hyperfattyacidemia, hepatic steatosis, non-alcoholic steatohepatitis, cirrhosis, liver failure, and non-alcoholic fatty liver disease. Methods also include those wherein administration of a lipocalin is to treat disorders or conditions characterized by elevated lipid levels, such lipids including LDL-C, ApoB, VLDL-C, IDL-C, non-HDL-C, Lp(a), serum triglyceride, liver triglyceride, Ox-LDL-C, small LDL particles, small VLDL, phospholipids, and oxidized phospholipids.

Without wishing to be bound by theory, administration of a lipocalin to an individual suffering from an LCN13-related condition is treated by improving insulin sensitivity and glucose metabolism (e.g., by improving insulin sensitivity in adipocytes, muscle cells, and/or liver cells), by suppressing hepatic glucose suppression, by suppressing hepatic lipogenesis in primary hepatocytes, and/or by promoting fatty acid β oxidation in primary hepatocytes.

Compositions and Formulations

The optimal lipocalin formulation will be determined by one of skill in the art depending on the route of administration and the desired dosage. Such formulations may influence the physical state, stability, rate of in vivo release and rate of in vivo clearance of the administered agents.

Besides those representative lipocalin dosage forms described herein, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey.

Pharmaceutical compositions comprising a lipocalin for use in accordance with the present invention are formulated in a conventional manner using one or more physiologically acceptable carriers comprising excipients and auxiliaries which facilitate processing of a therapeutic composition into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen.

When a therapeutically effective amount of a lipocalin composition is administered by e.g., intradermal, cutaneous or subcutaneous injection, the composition is, in one aspect, in the form of a pyrogen-free, parenterally acceptable aqueous solution. The preparation of such parenterally acceptable protein or polynucleotide solutions, having due regard to pH, isotonicity, stability, and the like, is within the skill in the art. A composition optionally contains, in addition to a lipocalin or other active ingredient of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The lipocalin composition, in another aspect, also contains stabilizers, preservatives, buffers, antioxidants, or other additives known to those of skill in the art. The agents of the invention are formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

The lipocalin formulations are, in certain aspects, designed to be short-acting, fast-releasing, long-acting, or sustained-releasing as described below. Thus, one type of pharmaceutical formulations is formulated for controlled release or for slow release. The instant lipocalin compositions, in other aspects, comprise, for example, micelles or liposomes, or some other encapsulated form, or may be administered in an extended release form to provide a prolonged storage and/or delivery effect. Therefore, the pharmaceutical lipocalin formulations are optionally compressed into pellets or cylinders and implanted intramuscularly or subcutaneously as depot injections or as implants such as stents. Such implants may employ known inert materials such as silicones and biodegradable polymers.

For oral administration, the compositions can be formulated readily by combining the active compounds with pharmaceutically acceptable carriers well known in the art. Such carriers enable the compounds of the invention to be formulated as tablets, pills, dragees, powders, capsules, liquids, solutions, gels, syrups, slurries, suspensions and the like, for oral ingestion by a patient to be treated.

For administration by inhalation, the compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas.

Compositions comprising a lipocalin for parenteral administration include aqueous solutions of the compositions in water-soluble form. Optionally, the suspension may also contain suitable stabilizers or agents which increase the solubility of the compositions to allow for the preparation of highly concentrated solutions. Alternatively, the active ingredient may be in powder form for constitution with a suitable vehicle, e.g., sterile pyrogen-free water, before use.

The compositions may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

The compositions also may comprise suitable solid or gel phase carriers or excipients.

The compositions of the invention may be in the form of a complex of the protein(s) or other active ingredient of present invention along with protein or peptide antigens.

The compositions may include a matrix capable of delivering the protein-containing or other active ingredient-containing composition to the site of tissue damage, providing a structure for the developing bone and cartilage and optimally capable of being resorbed into the body. Such matrices may be formed of materials presently in use for other implanted medical applications. The choice of matrix material is based on biocompatibility, biodegradability, mechanical properties, cosmetic appearance and interface properties.

The composition may further contain other agents which either enhance the activity of the protein or other active ingredient or complement its activity or use in treatment. Such additional factors and/or agents may be included in the pharmaceutical composition to produce a synergistic effect with protein or other active ingredient of the invention, or to minimize side effects.

Techniques for formulation and administration of the therapeutic compositions of the instant application may be found in "Remington's Pharmaceutical Sciences," Mack Publishing Co., Easton, Pa., latest edition. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

Administration

Administration of on a lipocalin according to the methods provided will be via any route. Conventional routes of administration, e.g., parenterally, subcutaneous, intravenous, intradermal, intramuscular, intramammary, intraperitoneal, intrathecal, intraocular, retrobulbar, intrapulmonary, intratracheal instillation, bronchial instillation, aerosol, sublingual, oral, nasal, anal, vaginal, or transdermal delivery, or by surgical implantation at a particular site are contemplated. Specifically contemplated are methods including intravenous administration.

Treatment in a method provided, in various aspects, consists of a single dose or a plurality of doses over a period of time. Administration of the lipocalin is systemic or local, and may comprise a single site injection or infusion of a therapeutically-effective amount of the lipocalin protein composition. Alternatively, it is contemplated that the therapeutic lipocalin composition is delivered to the patient at multiple sites. Multiple administrations are rendered simultaneously or administered over a period of time. Also contemplated is additional therapy wherein a lipocalin is administered on a period basis, for example, daily, weekly, or monthly.

In certain embodiments, parenteral administration of the therapeutic compounds is carried out with an initial bolus followed by continuous infusion to maintain therapeutic circulating levels of drug product. Those of ordinary skill in the art will readily optimize effective dosages and administration regimens as determined by good medical practice and the clinical condition of the individual patient. Methods provided include those wherein the lipocalin is administered orally and by injection. In methods wherein the lipocalin is injected, the injection is intravenous or subcutaneous. In certain aspects, injection is with a depot forming composition, and in embodiments including depot formation, the depot forming composition is administered by implanting a suitable delivery device in the patient. In one aspect, the delivery device is implanted subcutaneously, and in certain aspects, the delivery device is a pump.

The frequency of dosing will depend on the pharmacokinetic parameters of the lipocalin and the routes of administration. Depending on the route of administration, a suitable dose is calculated according to body weight, body surface areas or organ size. The availability of animal models is particularly useful in facilitating a determination of appropriate dosages of a given therapeutic.

Further refinement of the calculations necessary to determine the appropriate treatment dose is routinely made by those of ordinary skill in the art without undue experimentation. The final dosage regimen will be determined by the attending physician, considering factors which modify the action of the lipocalin, e.g., the specific activity, the responsiveness of the patient, the age, condition, body weight, sex and diet of the patient, the severity of any condition, time of administration, kind of concurrent treatment, if any, frequency of treatment, and the nature of the effect desired, and other clinical factors. As studies are conducted, further information will emerge regarding appropriate dosage levels and duration of treatment for specific diseases and conditions.

In certain embodiments, the lipocalin is administered alone, in other embodiments the lipocalin is administered in conjunction with other therapeutics directed to the target condition or directed to other symptoms thereof. Dosage levels of the order from about 0.01 mg to 30 mg per kilogram of body weight per day, for example from about 0.1 mg to 10 mg/kg.

Unit dosages of a lipocalin are also provided. "Unit dose" is defined as a discrete amount of a therapeutic composition dispersed in a suitable carrier.

It will be appreciated that the lipocalin and treatment methods provided are useful in fields of human medicine and veterinary medicine. Thus, the subject to be treated is a mammal, such as a human or other mammalian animal. For veterinary purposes, subjects include for example, farm animals including cows, sheep, pigs, horses and goats, companion animals such as dogs and cats, exotic and/or zoo animals, laboratory animals including mice rats, rabbits, guinea pigs and hamsters; and poultry such as chickens, turkey ducks and geese. The patient being treated is of any age, for example, between the ages of 10-50 years, age 20 or less, or age 10 or less.

In addition, it is contemplated that the lipocalins of the present invention are used in combination with any present treatments for LCN13-related disorders. For example, in certain embodiments, it is contemplated that the methods of the invention are useful in combination with known metabolic disorder, cardiovascular disorder and/or elevated lipid disorder therapy. Compositions comprising a lipocalin, or a fragment are administered before, after or during such therapy.

Combination Therapy

In order to increase the effectiveness of a treatment with the lipocalin compositions provided, it is in one aspect desirable to combine these compositions with other therapies effective in the treatment of specific diseases or conditions.

In some cases, the compositions of the present invention precede or follow the other agent treatment by intervals ranging from minutes to weeks. It is contemplated that one administers both modalities within about 12-24 h of each other or within about 6-12 h of each other. In some situations, it is desirable to extend the time period for treatment significantly, where several days (2, 3, 4, 5, 6 or 7) to several weeks (1, 2, 3, 4, 5, 6, 7 or 8) lapse between the respective administrations.

In certain specific instances lipocalin compositions are administered in combination with a second agent to prevent or treat a metabolic disorder or to prevent or treat a cardiovascular disease. For examples, agents that are useful in combination therapies include, but are not limited to, blood sugar-lowering agents (i.e., agents that lower blood sugar) or lipid-lowering agents (i.e., agents that reduce lipid levels).

Blood Sugar-Lowering Agents

Currently, there are various pharmacological approaches for the treatment of Type 2 diabetes. They act via different modes of action: 1) sulfonylureas (e.g., glimepiride, glisentide, sulfonylurea, AY31637) essentially stimulate insulin secretion; 2) biguanides (e.g., metformin) act by promoting glucose utilization, reducing hepatic glucose production and diminishing intestinal glucose output; 3) alpha-glucosidase inhibitors (e.g., acarbose, miglitol) slow down carbohydrate digestion and consequently absorption from the gut and reduce postprandial hyperglycemia; 4) thiazol-idinediones (e.g., troglitazone, pioglitazone, rosiglitazone, glipizide, balaglitazone, rivoglitazone, netoglitazone, troglitazone, englitazone, AD 5075, T 174, YM 268, R 102380, NC 2100, NIP 223, NIP 221, MK 0767, ciglitazone, adaglitazone, CLX 0921, darglitazone, CP 92768, BM 152054) enhance insulin action, thus promoting glucose utilization in peripheral tissues; 5) glucagon-like-peptides and agonists (e.g. exendin) or stabilizers thereof (e.g. DPP4 inhibitors, such as sitagliptin) potentiate glucose-stimulated insulin secretion; and 6) insulin or analogues thereof (e.g. LANTUS®) stimulate tissue glucose utilization and inhibits hepatic glucose output. The above mentioned pharmacological approaches may be utilized individually or in combination therapy.

Lipid-Lowering Agents

The term "lipid-lowering agent" refers to a pharmaceutical agent provided to a individual to achieve a lowering of lipids in the individual. For example, in certain embodiments, a lipid-lowering agent is provided to an individual to reduce one or more of LDL-C, ApoB, VLDL-C, IDL-C, non-HDL-C, Lp(a), serum triglyceride, liver triglyceride, Ox-LDL-C, small LDL particles, small VLDL, phospholipids, and oxidized phospholipids. Ideally, administration of a lipid-lowering agent leads to a reduction of one or more serum lipids in an individual over time.

In certain such embodiments, lipid-lowering pharmaceutical agents that may be co-administered with a pharmaceutical composition of the present invention include, but are not limited to atorvastatin, simvastatin, rosuvastatin, pravastatin, fluvastatin, and ezetimibe. In certain such embodiments, the lipid-lowering agent is administered prior to administration of a pharmaceutical composition of the present invention. In certain such embodiments, the lipid-lowering agent is administered following administration of a pharmaceutical composition of the present invention. In certain such embodiments the lipid-lowering agent is administered at the same time as a pharmaceutical composition of the present invention. In certain such embodiments the dose of a co-administered lipid-lowering agent is the same as the dose that would be administered if the lipid-lowering agent was administered alone. In certain such embodiments the dose of a co-administered lipid-lowering agent is lower than the dose that would be administered if the lipid-lowering agent was administered alone. In certain such embodiments the dose of a co-administered lipid-lowering agent is greater than the dose that would be administered if the lipid-lowering agent was administered alone.

Kits

The present invention also contemplates kits for use in the treatment of an LCN13-related disorder. Such kits include at least a first sterile composition comprising a lipocalin described above in a pharmaceutically acceptable carrier. Another component is optionally a second therapeutic agent for the treatment of the disorder along with suitable container and vehicles for administrations of the therapeutic compositions. The kits optionally comprise solutions or buffers for suspending, diluting or effecting the delivery of the first and second compositions. The kits also optionally comprise catheters, syringes or other delivering devices for the delivery of one or more of the compositions used in the methods of the invention. In another aspect, the kits optionally further comprise instructions containing administration protocols for the therapeutic regimens.

Methods of Diagnosing LCN13-Related Conditions

The present disclosure also contemplates methods of diagnosing an LCN13-related condition in a patient comprising determining lipocalin (e.g., LCN13, LCN1, LCN3, LCN4, LCN14, OBP2B, and OBP2A) levels in a sample from the patient suspected of suffering from an LCN13-related condition.

It will be appreciated that determination of the level of a lipocalin in a patient sample will be useful in determining how to manage the LCN13-related condition in the patient. For example, since reduced levels of LCN13 are associated with metabolic disorders and cardiovascular diseases, the clinician may use the information concerning the levels of LCN13 to facilitate decision making regarding treatment of the patient. Thus, if the level of LCN13 is indicative of an early stage of an LCN13-related condition, appropriate treatment regimens may be prescribed.

The level of lipocalin which is indicative of an LCN13-related condition may be defined as the decreased level present in samples from individuals known to have an LCN13-related condition over the lipocalin level in samples from individuals known to be free of an LCN13-related condition. The level of lipocalin may be, for example, at least 1.1 fold, 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 3.6 fold, 3.7 fold, 3.8 fold, 3.9 fold, 4.0 fold, 4.1 fold, 4.2 fold, 4.3 fold, 4.4 fold, 4.5 fold, 4.6 fold, 4.7 fold, 4.8 fold, 4.9 fold, 5.0 fold, 5.1 fold, 5.2 fold, 5.3 fold, 5.4 fold, 5.5 fold, 5.6 fold, 5.7 fold, 5.8 fold, 5.9 fold, or 6.0 fold lower in a sample from an individual with an LCN13-related condition.

It will be appreciated that the methods of the invention include methods which aid diagnosis and methods of prognosis. It will also be appreciated that the methods of the invention are useful to the physician in determining a course of management or treatment of the patient.

The lipocalin markers identified using the methods provided are, in one aspect, used to evaluate treatment efficacy (e.g., amelioration of one or more symptoms of a pathology). Where the amelioration of an LCN13-related condition can be related to an increase in levels of a lipocalin, lipocalin levels in a sample taken from the patient are measured before (for background) and during or after (e.g., at a designated time, periodically or randomly) the course of treatment. Because an increase in lipocalin levels may be transient, the method is, in one aspect, performed at regular intervals, (e.g., every 6 hours, every 12 hours, every 18 hours, every 24 hours, every 2 days, every 3 days, every 4 days, every 5 days, every 6 days, every 7 days, every 8 days, every 9 days, every 10 days, every 11 days, every 12 days, every 13 days, every 2 weeks, every 3 weeks, every 4 weeks, every 5 weeks, every 6 weeks, every 7 weeks, every 2 months, every 3 months, every 4 months, every 5 months, every 6 months, every 7 months, every 8 months, every 9 months, every 10 months, every 11 months, every year, or more) closely before and after each treatment. Depending on the course of treatment and other clinical variables, clinicians of ordinary skill in the art will be able to determine an appropriate schedule for performing the assay for diagnostic or disease/treatment monitoring purposes.

In various embodiments, the lipocalin protein is detected and/or quantified in the sample using any of a number of well recognized immunological binding assays (see, e.g., U.S. Pat. Nos. 4,366,241; 4,376,110; 4,517,288; and 4,837,168). For a review of general immunoassays, see also Methods in Cell Biology Volume 37: Antibodies in Cell Biology, Asai, ed. Academic Press, Inc. New York (1993); Basic and Clinical Immunology 7th Edition, Stites & Terr, eds. (1991).

In another embodiment, immunoblot (Western blot) analysis is used to detect and quantify the presence of a lipocalin in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the lipocalin. The anti-lipocalin antibodies specifically bind to the lipocalin on the solid support. These antibodies may be directly labeled or alternatively may be subsequently detected using labeled antibodies (e.g., labeled sheep anti-mouse antibodies) that specifically bind to the anti-lipocalin antibody.

In another embodiment, quantitative assays of a lipocalin are deemed to show a positive result, e.g., elevated or decreased lipocalin level, when the measured lipocalin level is greater or less than the level measured or known for a control sample (e.g. either a level known or measured for a normal healthy individual or a "baseline/reference" level determined at a different time for the same individual. In a particularly preferred embodiment, the assay is deemed to show a positive result when the difference between sample and "control" is statistically significant (e.g. at the 85% or greater, preferably at the 90% or greater, more preferably at the 95% or greater and most preferably at the 98% or greater confidence level).

In one embodiment of the disclosure, antibodies immunoprecipitate lipocalin proteins from solution as well as react with lipocalin protein on western or immunoblots of polyacrylamide gels. In another embodiment, antibodies detect lipocalin proteins in stored serum samples.

EXAMPLES

The following examples are provided for illustration and are not in any way to limit the scope of the invention.

Example 1

Obesity is Associated with Reduced Expression and Secretion of LCN13

Generation of LCN13 Adenoviruses

A full-length of LCN13 cDNA was inserted 3' prime of the CMV promoter sequences in an adenoviral vector and used to generate recombinant LCN13 adenoviruses using pAdEasy kits (QBiogene, Carlsad, Calif.). Recombinant adenoviruses were amplified in QBI-293A cells and purified by CsCl gradient ultracentrifugation. LCN13 or (β-galactosidase ((β-gal) (control) adenoviruses were administered into mice via tail vein injection at $2 \times 10^{11}$ viral particles per mouse.

Immunoprecipitation and Immunoblotting

Tissues were homogenized in lysis buffer (50 mM Tris, pH 7.5; 1% Nonidet P-40; 150 mM NaCl; 2 mM EGTA; 1 mM $Na_3VO_4$; 100 mM NaF; 10 mM $Na_4P_2O_7$; 1 mM benzamidine; 10 µg/ml aprotinin; 10 µg/ml leupeptin; 1 mM phenylmethylsulfonyl fluoride). Tissue extracts were incubated with primary antibodies at 4° C. for 2 h and with protein A-agarose beads (RepliGen Corp., Waltham, Mass.) for an additional hour at 4° C. The immunocomplexes absorbed on the protein A-agarose beads were washed three times with washing buffer (50 mM Tris, pH 7.5; 1% Nonidet P-40; 150 mM NaCl; 2 mM EGTA) and boiled at 95° C. for 5 mM in loading buffer (50 mM Tris-HCl, pH 6.8; 2% SDS, 2% β-mercaptoethanol; 10% glycerol; 0.005% bromphenol blue). Protein was separated by SDS-PAGE, immunoblotted with indicated antibodies, and visualized using the Odyssey Infrared Imaging System (Li-Cor Biosciences, Lincoln, Nebr.) or ECL (Amersham, Piscataway, N.J.). Polyclonal anti-LCN13 antibodies were raised against glutathione-S-transferase-LCN13 fusion protein. Phospho-Akt (Thr$^{308}$), Akt and insulin receptor β subunit antibodies were from Santa Cruz (Santa Cruz, Calif.). Anti-phospho-tyrosine antibody was from Upstate (Billerica, Mass.). AntiphosphoAkt (Ser$^{473}$) antibody was from Invitrogen (Carlsbad, Calif.).

Quantitative Real-Time RT-PCR (qRT-PCR)

Total RNA was extracted from the liver or hepatocytes and used to synthesize the first strand cDNAs using oligo(dT)$_{12-18}$ and Moloney murine leukemia virus reverse transcriptase. The mRNA abundance of various molecules was measured using Absolute QPCR SYBR Green kits (Thermo Scientific, Waltham, Mass.) and the Mx3000P real-time PCR system (Stratagene, La Jolla, Calif.). Primers for qRT-PCR were: LCN13 forward: 5'-GTCATTCGGGATGGGAAAG-3' (SEQ ID NO: 2), LCN13 reverse: 5'-GCTGTTGCAGAC-CTGGGTA-3' (SEQ ID NO: 3); β-actin forward: 5'-AAATCGTGCGTGACATCAAA-3' (SEQ ID NO: 4), β-actin reverse: 5'-AAGGAAGGCTGGAAAAGAGC-3' (SEQ ID NO: 5); PEPCK forward: 5'-ATCATCTTTGGTG-GCCGTAG-3' (SEQ ID NO: 6), PEPCK reverse: 5'-ATCT-TGCCCTTGTGTTCTGC-3' (SEQ ID NO: 7); G6Pase forward: 5'-CCGGTGTTTGAACGTCATCT-3' (SEQ ID NO: 8), G6Pase reverse: 5'-CAATGCCTGACAAGACTCCA-3' (SEQ ID NO: 9); PGC-1α forward: 5'-TGGACGGAAG-CAATTTTTCA-3' (SEQ ID NO: 10), PGC-1α reverse: 5'-TTACCTGCGCAAGCTTCTCT-3' (SEQ ID NO: 11); 36B4 forward: 5'-AAGCGCGTCCTGGCATTGTCT-3' (SEQ ID NO: 12), 36B4 reverse: 5'-CCGCAGGGGCAG-CAGTGGT-3' (SEQ ID NO: 13); ChREBP forward: 5'-CTGGGGACCTAAACAGGAGC-3' (SEQ ID NO: 14), ChREBP reverse: 5'-GAAGCCACCCTATAGCTCCC-3' (SEQ ID NO: 15); CPT1α forward: 5'-CTGATGACGGC-TATGGTGTTT-3' (SEQ ID NO: 16), CPT1α reverse: 5'-GT-GAGGCCAAACAAGGTGATA-3' (SEQ ID NO: 17); FAS forward: 5'-TTGACGGCTCACACACCTAC-3' (SEQ ID NO: 18), FAS reverse: 5'-CGATCTTCCAGGCTCTTCAG-3' (SEQ ID NO: 19); LCAD forward: 5'-CACTCAGATAT-TGTCATGCCCT-3' (SEQ ID NO: 20), LCAD reverse: 5'-TCCATTGAGAATCCAATCACTC-3' (SEQ ID NO: 21); MCAD forward: 5'-ACCCTGTGGAGAAGCTGATG-3' (SEQ ID NO: 22), MCAD reverse: 5'-AGCAACAGTGCT-TGGAGCTT-3' (SEQ ID NO: 23); PPARγ forward: 5'-CCA-GAGTCTGCTGATCTGCG-3' (SEQ ID NO: 24), PPARγ reverse: 5'-GCCACCTCTTTGCTCTGATC-3' (SEQ ID NO: 25); SCD1 forward: 5'-AGGTGCCTCTTAGCCACTGA-3' (SEQ ID NO: 26), SCD1 reverse: 5'-CCAGGAGTTTCT-TGGGTTGA-3' (SEQ ID NO: 27); SREBP1c forward 5'-AACGTCACTTCCAGCTAGAC-3' (SEQ ID NO: 28), SREBP1c reverse 5'-CCACTAAGGTGCCTACAGAGC-3' (SEQ ID NO: 29).

Results

To examine tissue distribution of LCN13, total RNAs were prepared from various tissues and used to specifically amplify LCN13 by reverse transcription PCR using primers unique to LCN13. LCN13 mRNA was detected in multiple tissues, including livers, skeletal muscle, the pancreas and white adipose tissue (WAT) (FIG. 1A). To measure the levels of endogenous LCN13 protein, anti-LCN13 antibody (αLCN13) was raised against glutathione S-transferase-LCN13 fusion protein. Tissue extracts were prepared and immunoblotted with αLCN13. Two isoforms of LCN13 were detected in the liver, skeletal muscle and WAT, but at relatively low levels in the last two tissues (FIG. 1B).

To determine whether LCN13 is a secretary protein, a full-length of mouse LCN13 cDNA was inserted into an adenoviral vector under the control of the CMV promoter. FAO cells (rat hepatoma cells) were infected with LCN13 or β-gal adenoviruses. Culture medium was collected 48 h after infection and immunoblotted with αLCN13. Two isoforms of LCN13 were detected in the medium from LCN13 but not β-gal adenovirus-infected cells (FIG. 1C, right two lanes). LCN13 was also detected in cell extracts prepared from LCN13 but not β-gal adenovirus-infected cells (FIG. 1C, left two lanes). These results indicate that LCN13 was secreted as two isoforms, presumably due to differential proteolytic cleavages.

To determine whether LCN13 is present in the bloodstream, plasma was prepared from fasted (16 h) or randomly fed mice and immunoblotted with αLCN13. LCN13 was detected in the blood; interestingly, fasting reduced plasma LCN13 levels (FIG. 1D). To determine whether circulating LCN13 levels are altered in obesity, plasma was prepared either from male mice fed a standard chow and high fat diet (HFD) or from leptin-deficient ob/ob and wild type littermates. The plasma was immunoprecipitated with αLCN3 and immunoblotted with αLCN3. Circulating LCN13 was dramatically reduced in mice with either genetic (ob/ob) or dietary fat-induced obesity (FIG. 1E). In agreement with these observations, LCN13 expression markedly decreased in the livers of mice with HFD-induced obesity (FIG. 1F). These results suggest that LCN13 deficiency contributes to insulin resistance and glucose intolerance in obese mice.

Example 2

Transgenic Expression of LCN13 Protects Against HFD-Induced Insulin Resistance and Glucose Intolerance Generation of LCN13 Transgenic Mice.

The LCN13 transgene constructs were engineered by inserting a full-length mouse LCN13 cDNA into a pCAGGS vector (FIG. S2A). A "stop" cassette, which was flanked by two loxp sites, was inserted between the chicken β-actin/rabbit β-globin hybrid promoter and the LCN13 cDNA. The transgenic constructs were linearized with SalI and ApL1, purified, and microinjected into F2 mouse oocytes (in C57BL/6 background). The oocytes were surgically transferred to recipients in the University of Michigan Transgenic Animal Model Core. Transgenic animals were identified by PCR-based genotyping assays. The transgenic mice were crossed with EIIA-Cre mice (in C57BL/6 genetic background) to generate LCN13 and EIIA-Cre double-transgenic mice. Cre was expressed in the germ cells of the LCN13/EHA-Cre double-transgenic mice and deleted the "STOP" cassette via the two loxp sites; therefore, the progenies of the LCN13/EIIA-Cre transgenic mice were predicted to express the LCN13 transgene under the control of the chicken β-actin/rabbit β-globin hybrid promoter. This hybrid promoter is constitutively active in multiple tissues of the transgenic mice. The EIIACre transgene was removed by a series of backcross of the LCN13/EIIA-Cre transgenic mice with wild type mice (in C57BL/6 background). We obtained two independent lines of LCN13 transgenic mice: LCN13-642 and LCN13-783.

ob/ob and db/db mice (in C57BL/6 background) were from the Jackson Laboratory (Bar Harbor, Me.). Mice were housed on a 12-h light and 12-h dark cycle in the Unit for Laboratory Animal Medicine at the University of Michigan (ULAM), and fed either normal chow (9% fat; Lab Diet) or HFD (45% fat; Research Diets) ad libitum with free access to water. Animal experiments were conducted following protocols approved by the University Committee on the Use and Care of Animals (UCUCA).

Animal Experiments

Blood samples were collected from mouse tail veins using heparin-pretreated capillary tubes. Blood glucose was measured by a glucometer (Bayer Corp., Tarrytown, N.Y.), and plasma insulin was measured using a rat insulin enzyme-linked immunosorbent assay kit (Crystal Chem, Inc., Chicago, Ill.). HOMA index was calculated as: fasting blood glucose (mmol/l)×fasting plasma insulin (μU/ml)/22.5.

For glucose tolerance tests (GTT), mice were fasted overnight (16 h) and intraperitoneally injected with D-glucose. Blood glucose was measured 0, 15, 30, 60, and 120 min after glucose injection. For insulin tolerance tests (ITT), mice were fasted for 6 h (from 10:00 a.m. to 4:00 p.m.) and intraperitoneally injected with human insulin. Blood glucose was monitored 0, 15, 30, and 60 min after insulin injection.

Results

To determine whether LCN13 regulates insulin sensitivity and glucose metabolism, a full-length mouse LCN13 cDNA was inserted into a transgenic construct under the control of the chicken β-actin/rabbit β-globin hybrid promoter and used to generate LCN13 transgenic mice. This hybrid promoter is constitutively active in multiple mouse tissues. Two independent lines (LCN13-783 and LCN13-642) were generated and used in the following experiments. Circulating LCN13 levels were higher in LCN13 transgenic mice than in wild type (WT) littermates (FIG. 2A). LCN13 overexpression did not alter body weight in both LCN13-783 and LCN13-642 mice.

LCN13-783 and WT male littermates (7 weeks) were fed a HFD. Chronic overexpression of LCN13 protected against HFD-induced hyperglycemia and insulin resistance (FIGS. 2B-E). Plasma insulin decreased by 47% in LCN13-783 mice (FIG. 2B). HOMA index, which is commonly used to estimate insulin sensitivity, decreased by 63% in LCN13-783 mice (FIG. 2C). To further analyze insulin sensitivity and glucose metabolism, LCN13-783 and WT littermates were fed a HFD for 12 weeks and subjected to insulin tolerance tests (ITT) and glucose tolerance tests (GTT). Exogenous insulin reduced blood glucose levels to a greater extent in LCN13-783 than in WT littermates (FIG. 2D). Glucose injection increased blood glucose in both LCN13-783 and WT mice, but to a much lower level in LCN13-783 than in WT littermates (FIG. 2E). Chronic overexpression of LCN13 also protected against HFD-induced glucose intolerance in LCN13-642 line (FIG. 2F).

Example 3

LCN13 Attenuates Insulin Resistance, Hyperglycemia, and Glucose Intolerance in Mice with Type 2 Diabetes Plasma LCN13 levels were markedly reduced in obese, insulin resistant mice (FIG. 1E). To determine whether restoration of circulating LCN13 improves insulin resistance and glucose intolerance in mice with type 2 diabetes, db/db mice, which serve as a genetic model of obesity and type 2 diabetes, were infected with LCN13 or β-gal adenoviruses via tail vein injection. Recombinant adenoviruses primarily infect liver cells under these conditions. Recombinant LCN13 was detected as two isoforms in the livers of LCN13 but not β-gal adenovirus-infected mice (FIG. 3A). These results support the observations in FIGS. 1B-C that two isoforms of LCN13 are generated from proteolytic cleavages of a LCN13 precursor. Plasma LCN13 levels were also significantly elevated in LCN13 adenovirus-infected mice (FIG. 3A).

Restoration of LCN13 markedly improved both hyperglycemia and hyperinsulinemia in db/db mice (FIG. 3B). In LCN13 adenovirus-infected mice, blood glucose and plasma insulin decreased by 46% and 51%, respectively. In GTT, glucose injection increased blood glucose levels to a lesser extent in LCN13 adenovirus-infected mice than in β-gal adenovirus-infected mice (FIG. 3C). In ITT, blood glucose levels were significantly lower in LCN13 than in β-gal adenovirus-infected mice at each time point after insulin injection (FIG. 3D). These data indicate that restoration of circulating LCN13 largely reverses hyperglycemia, hyperinsulinemia, and glucose intolerance in type 2 diabetes.

Figure 4B:
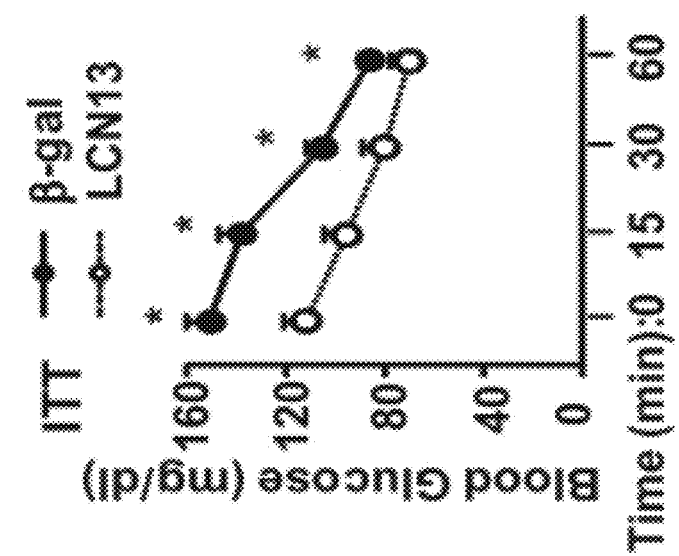
Figure 4C:
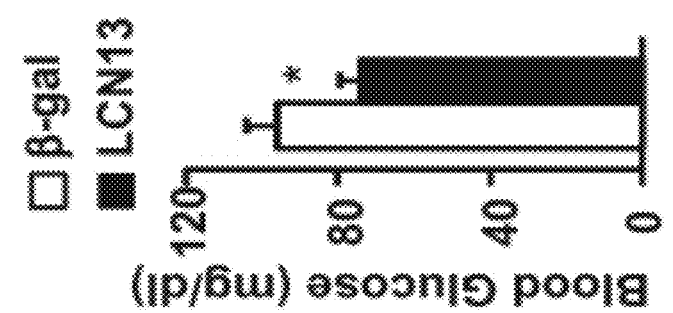

To determine whether LCN13 overexpression reverses insulin resistance and glucose intolerance in dietary fat-induced type 2 diabetes, C57BL/6 mice were fed a HFD for 10 weeks and infected with LCN13 or β-gal adenoviruses. Fasting blood glucose levels were 29% lower in LCN13 than in β-gal adenovirus-infected mice (FIG. 4A). In ITT, blood glucose levels were also lower in LCN13 than in 0-gal adenovirus-infected mice at each time point after insulin injection (FIG. 4B). Adenovirus-expressed LCN13 also improved glucose intolerance in HFD-fed mice (FIG. 4C). Taken together, these data suggest that liver-specific overexpression of LCN13 attenuated insulin resistance, hyperglycemia and glucose intolerance in both genetic and diet-induced type 2 diabetes.

Figure 5A:
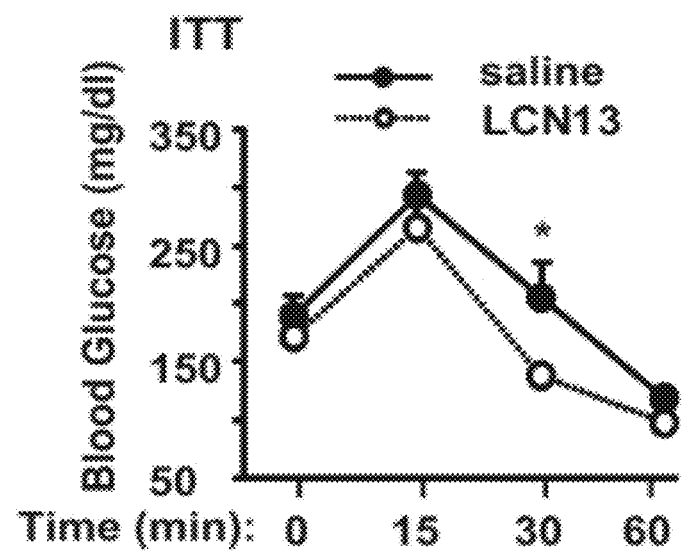
FIGS. 5A and 5B illustrate experimental results indicating that purified LCN13 improves insulin sensitivity and glucose metabolism in ob/ob mice. An LCN13 cDNA fragment, which lacks the sequence encoding the secretory signal peptide (amino acids 1-18), was inserted into pET28a(+) bacterial expression vector to generate N-terminal His6 tagged-LCN13. The vector was transformed into E. coli BL21 cells, and His$_6$-LCN13 was purified using a Ni$^{2+}$-nitrilotriacetic acid column (Qiagen, Valencia, Calif.) following manufacturer's instructions. Endotoxins were removed using Detoxi-Gel™ endotoxin removal kits (Thermo Scientific, Rockford, Ill.). ob/ob mice (10 weeks) were anesthetized with 2-4% isoflurane and osmotic minipumps (Model 2002, Alzet, Cupertino, Calif.) were implanted subcutaneously at the dorsum of the neck. Minipumps were pre-filled with either sterile 0.9% NaCl vehicle or His$_6$-LCN13 dissolved in vehicle. LCN13-filled pumps released His$_6$-LCN13 at 33 pmol/h/mouse. (A) ITT was performed on mice 10 days after the treatments (insulin: 4 U/kg body weight). (B) GTT was performed on mice 12 days after the treatments (D-glucose: 0.5 g/kg body weight). Error bars represent SEM. Error bars represent SEM. *P<0.05.
Figure 5B:
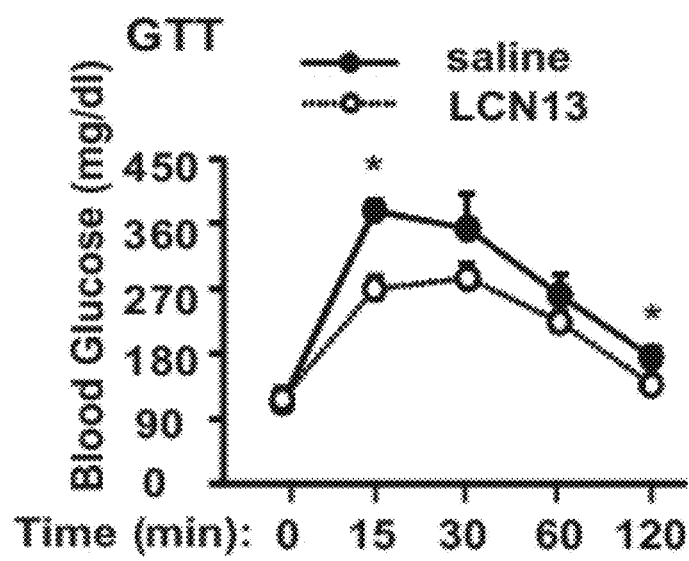

To determine whether purified LCN13 regulates glucose metabolism, mouse LCN13 was N-terminally $His_6$-tagged and purified from bacteria. ob/ob mice (10 weeks) were chronically administrated with vehicles or purified LCN13 (33 pmol/h) via osmotic minipump. Insulin sensitivity was slightly improved 10 days after LCN13 treatment as revealed by ITT (FIG. 5A). Glucose intolerance was also improved 12 days after LCN13 treatments (FIG. 5B). However, the insulin sensitizing effect of purified LCN13 was relatively mild, presumably due to a low dose of LCN13 used in these experiments. Alternatively, bacteria-produced LCN13 may be improperly processed and folded, thus less active than LCN13 expressed by mammalian cells.

Example 4

LCN13 Promotes Insulin Signaling in HFD-Fed Mice

Figure 6A:
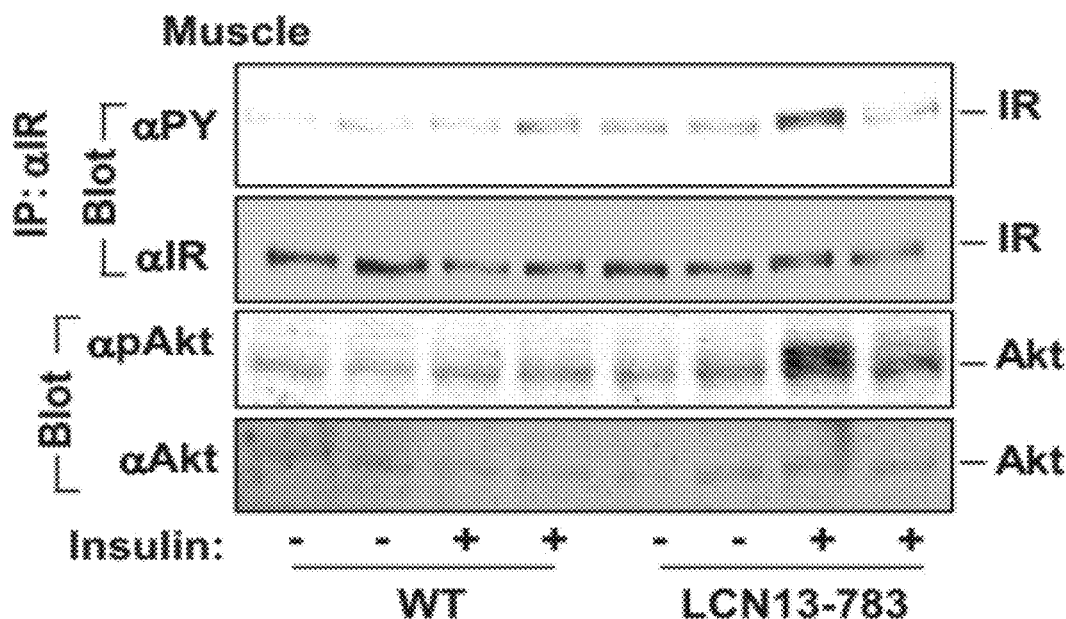
FIGS. 6A and 6B illustrate experimental results indicating that LCN13 enhances insulin signaling in LCN13 transgenic mice. LCN13-783 and WT male littermates (7 weeks) were fed HFD for 15 weeks. Mice were fasted for 16 hours and stimulated with insulin (3 U/kg body weight) or PBS. Tissue extracts were prepared 5 min after stimulation. (A) The insulin receptor in muscle extracts was immunoprecipitated with αIR and immunoblotted with anti-phosphotyrosine (αPY). Muscle extracts were also immunoblotted with αphospho-Akt (pSer$^{473}$) or αAkt, respectively. (B) Liver extracts were immunoblotted with αpSer$^{473}$ or αAkt, respectively.
Figure 6B:
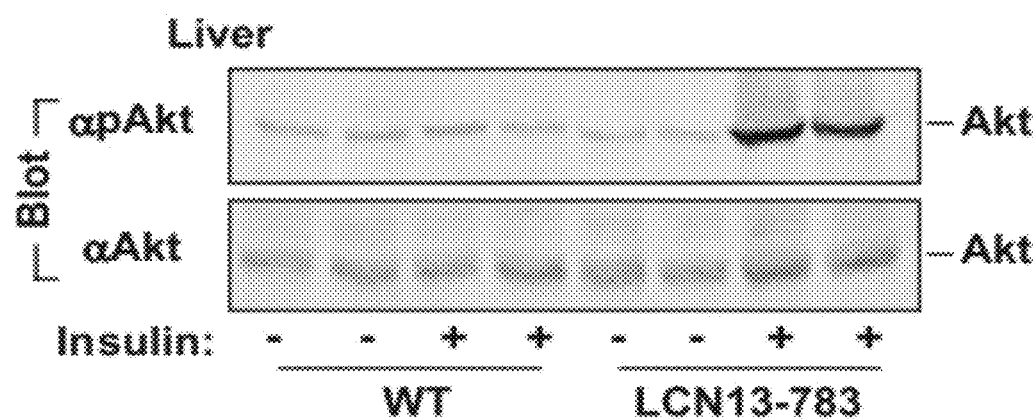

To examine the effect of chronic LCN13 treatments on insulin signaling, LCN13-783 and WT littermates were fed a HFD for 15 weeks. Mice were fasted overnight and treated with PBS or insulin (3 U/kg body weight). Tissue extracts were prepared 5 min after the treatments and used to measure phosphorylation of key components of the insulin pathways. Insulin only slightly stimulated tyrosine phosphorylation of the insulin receptor (IR) and phosphorylation of Akt ($pSer^{473}$) in the skeletal muscle of WT mice, indicating that HFD induces insulin resistance in WT mice (FIG. 6A). By contrast, insulin potently stimulated phosphorylation of both IR and Akt in LCN13-783 mice (FIG. 6A). Insulin was unable to stimulate Akt phosphorylation in the livers of WT mice, but robustly stimulated Akt phosphorylation in LCN13-783 mice (FIG. 6B). These results suggest that LCN13 is likely to improve glucose metabolism by increasing insulin sensitivity in animals.

Example 5

LCN13 Directly Promotes Insulin Action in Adipocytes

Adipocyte Differentiation and Glucose Uptake Assays
3T3-L1 preadipocytes were cultured in DMEM containing 25 mM glucose, 10% calf serum at 37° C. and 5% $CO_2$. Two days post-confluency, 3T3-L1 preadipocytes were cultured for 3 days in a differentiation medium (DMEM supplemented with 10% fetal bovine serum (FBS), 0.1 µM insulin, 1 µM dexamethasone, 0.5 mM 3-isobutyl-1-methylxanthine) and 3 additional days in DMEM supplemented with 10% FBS and 0.1 µM insulin. Differentiated adipocytes were maintained in DMEM supplemented with 10% FBS, and pretreated with purified LCN13 for the indicated times in DMEM supplemented with 0.6% bovine serum albumin (BSA). In glucose uptake assays, adipocytes were incubated with DMEM containing 0.6% BSA for 3 h, washed with Krebs-Ringer buffer (130 mM NaCl, 5 mM KCl, 1.3 mM $CaCl_2$, 1.3 mM $MgSO_4$, 25 mM HEPES, pH 7.4), and incubated with or without insulin for 30 min. [$^3$H]2-deoxy-D-glucose was added during the last 5 min of insulin stimulation. Cells were immediately washed three times with ice-cold PBS and solubilized in 0.1% SDS buffer. [$^3$H]2-deoxy-D-glucose uptake was determined by scintillation counting.

Figure 7A:
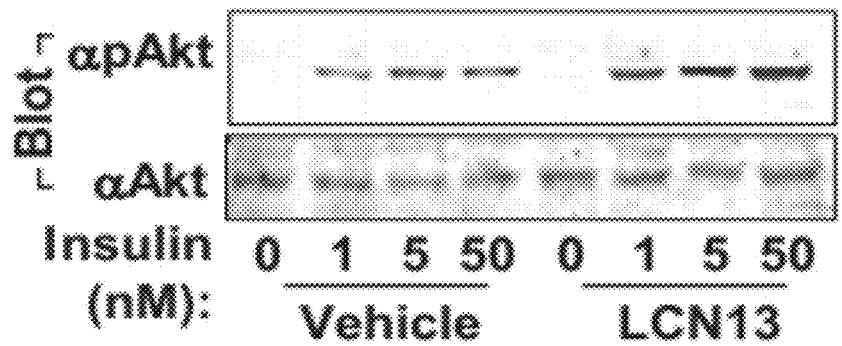
FIGS. 7A and 7B illustrate illustrates experimental results indicating that LCN13 directly enhances insulin sensitivity in adipocytes. (A) 3T3-L1 adipocytes were pretreated with 50 nM LCN13 or vehicles for 6 h and then treated with insulin for 10 min. Cell extracts were immunoblotted with αphospho-Akt (pThr$^{308}$) or αAkt, respectively. (B) 3T3-L1 adipocytes were pretreated with 50 nM LCN13 for the indicated times, and then treated with insulin or PBS (basal). 2-deoxyglucose uptake was measured. Error bars represent SEM. *P<0.05.
Figure 7B:
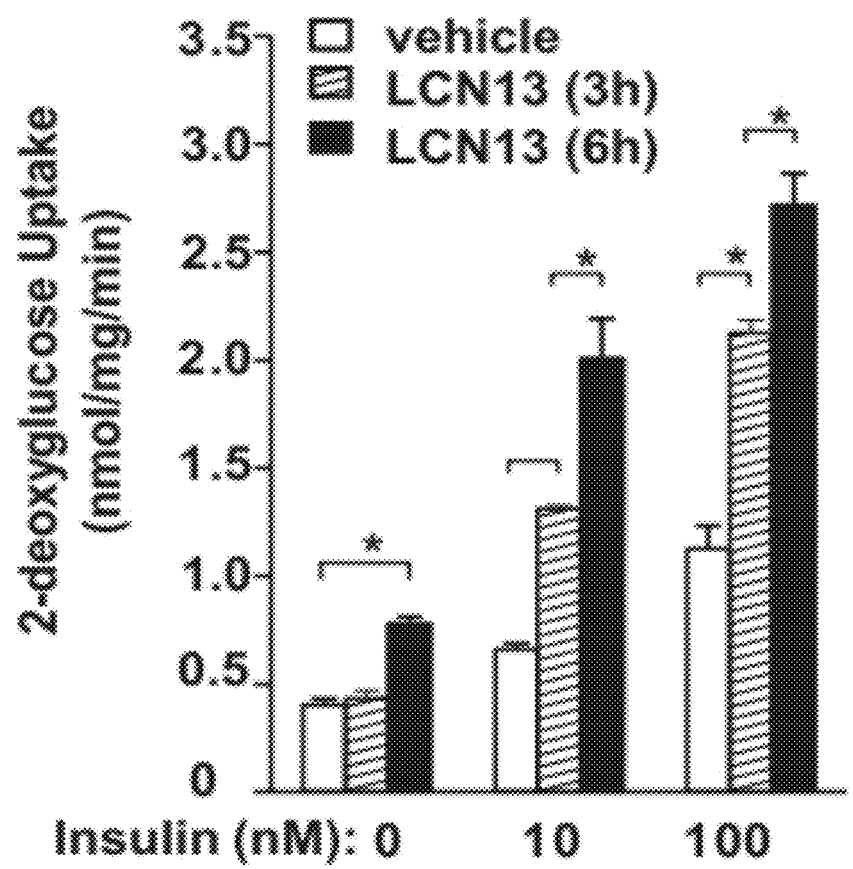

Results
To determine whether LCN13 directly enhances insulin signaling, 3T3-L1 adipocytes were pretreated with LCN13 or vehicles, and then stimulated with insulin. Cell extracts were immunoblotted with phospho-Akt antibodies. Insulin stimulated Akt phosphorylation, whereas LCN13 did not; however, LCN13 increased insulin-stimulated phosphorylation of Akt (FIG. 7A). To further determine whether LCN13 sensitizes insulin action, 3T3-L1 adipocytes were pretreated with LCN13 (100 nM) or vehicles for 3 or 6 h. The cells were subsequently stimulated with insulin, and glucose uptake was measured. LCN13 did not alter basal glucose uptake after LCN13 pretreatment for 3 h, but it markedly enhanced insulin stimulation of glucose uptake (FIG. 7B). Interestingly, LCN13 enhanced both basal and insulin-stimulated glucose uptake after LCN13 pretreatment for 6 h (FIG. 7B). These data suggest that LCN13 directly promotes glucose uptake in adipocytes by an insulin-dependent mechanism in the short-term and by both insulin-dependent and -independent mechanisms in the long-term.

Example 6

LCN13 Suppresses Hepatic Glucose Production by Both Insulin-Dependent and -Independent Mechanisms Hepatic Glucose Production (HGP) Assays
Mouse hepatocytes were isolated by liver-perfusion with type II collagenase (Worthington Biochem, Lakewood, N.J.) and grown on collagen-coated plates for 2 h in Williams' Medium E (Sigma, St. Louis, Mo.) containing 2% FBS, 100 units/ml penicillin and 100 µg/ml streptomycin. Cells were rinsed with PBS and cultured for an additional 4 h in KRB buffer (118 mM NaCl, 2.5 mM $CaCl_2$, 4.8 mM KCl, 25 mM $NaHCO_3$, 1.1 mM $KH_2PO_4$, 1.2 mM $MgSO_4$, 10 µM $ZnSO_4$, 0.6% BSA, 10 mM HEPES, pH 7.4) in the presence or absence of recombinant LCN13 protein. For HGP assays, primary hepatocyte cultures were washed twice with PBS and incubated with HGP buffer (KRB buffer supplemented with 10 mM sodium DL lactate and 5 mM pyruvate) in the presence or absence of 100 nM insulin or MIX (10 µM $N^6$,2'-O-dibutyryladenosine 3',5'-cyclic monophosphate sodium salt and 100 nM dexamethasone). Culture buffer was collected 4 h later and used to measure glucose using Glucose LiquiColor kits (Fisher Scientific Inc., Pittsburgh, Pa.).

Figure 8A:
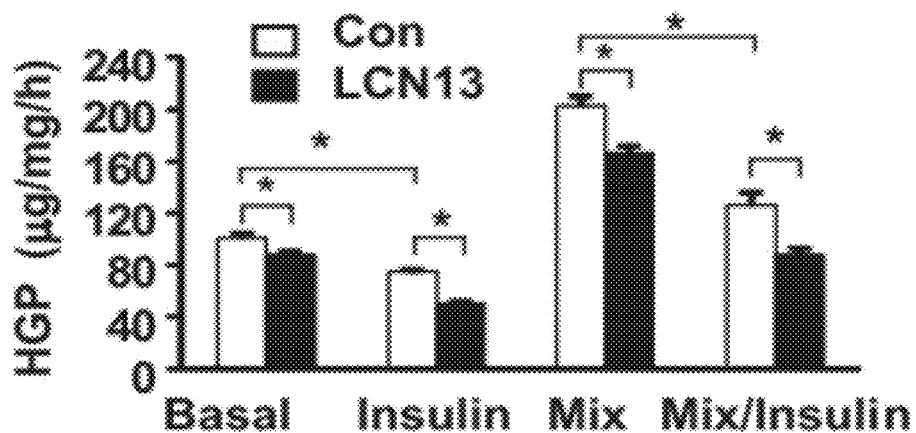
FIGS. 8A and 8B illustrate experimental results indicating that LCN13 suppresses hepatic glucose production by both insulin-dependent and -independent mechanisms. (A) Primary hepatocyte cultures were treated with 100 nM LCN13 or vehicles for 4 h and then subjected to hepatic glucose production (HGP) assays for additional 4 h in the presence of PBS (basal), 100 nM insulin (Ins), Mix (a combination of 10 μM N$^6$,2'-0-dibutyryladenosine 3',5'-cyclic monophosphate sodium salt and 100 nM dexamethasone), or both insulin and Mix. HGP was normalized to total protein levels. (B) Primary hepatocyte cultures were pretreated with 100 nM LCN13 or vehicles for 4 h and then treated with Mix or a combination of both mix and insulin for additional 4 h. The expression of key gluconeogenic genes were measured by qRT-PCR and normalized to β-actin expression. Error bars represent SEM. *P<0.05.

Results
LCN13 is expressed at relative high levels in the liver (FIGS. 1A-B). To determine whether LCN13 is involved in glucose metabolism in hepatocytes, primary hepatocyte cultures were pretreated with LCN13 for 4 h, and then subjected to hepatic glucose production (HGP) assays in the presence of PBS (basal), insulin, Mix (a combination of a cAMP analog and dexamethasone), or both insulin and Mix. Mix stimulated HGP by 102%; insulin suppressed both basal and Mix-stimulated HGP by 25% and 38%, respectively (FIG. 7A). Importantly, LCN13 alone also suppressed both basal (by 13%) and Mix-stimulated (18%) HGP (FIG. 8A). LCN13 and insulin act synergistically to further inhibit both basal (50%) and Mix-stimulated (56%) HGP (FIG. 8A).

Figure 8B:
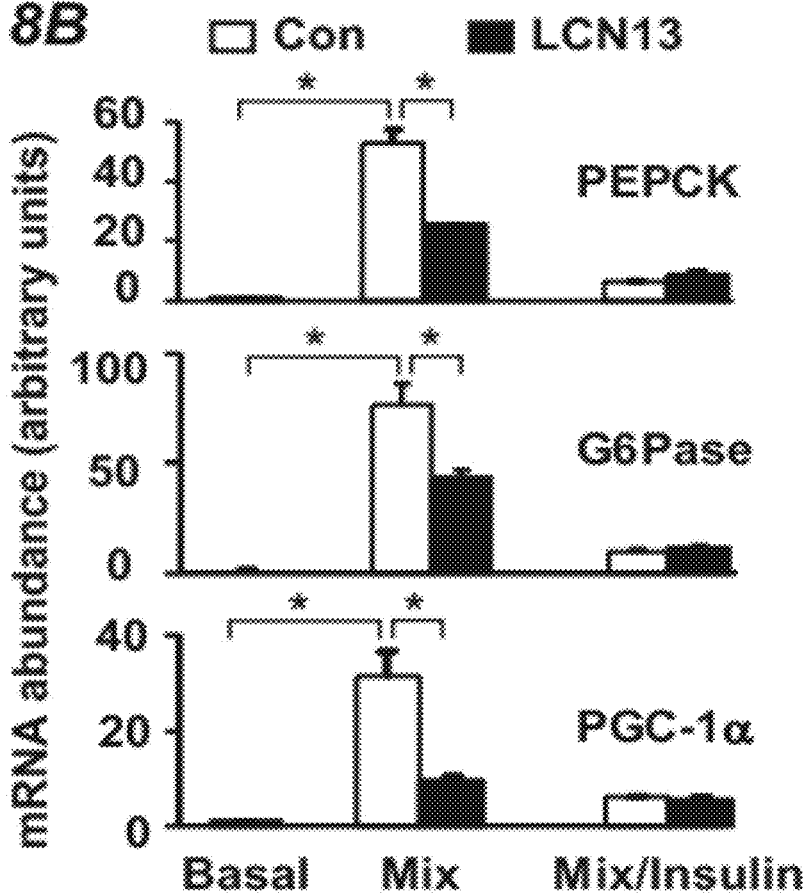

To determine whether LCN13 regulates the expression of the genes that control hepatic gluconeogenesis, primary hepatocyte cultures were pretreated with LCN13 and then treated with Mix or Mix plus insulin as described above. The expression of key gluconeogenic genes, including phosphoenolpyruvate carboxykinase (PEPCK), glucose-6-phostatase (G6Pase), and PGC-1a, were measured by quantitative real-time RT-PCR and normalized to β-actin expression. Mix potently stimulated the expression of PEPCK, G6Pase and PGC-1α; insulin suppressed Mix-stimulated expression of PEPCK (by 88%), G6Pase (86%) and PGC-1a (81%) (FIG. 8B). LCN13 alone also inhibited the expression of these genes, but to a lesser extent than insulin (FIG. 8B). Together, these data suggest that LCN13 is able to suppress HGP by both insulin-dependent and -independent mechanisms.

Example 7

LCN13 is Effective in Reducing Blood Cholesterol and Lipid Levels

LCN13 Decreases Blood Cholesterol Levels in Obese Mice.

Figure 9A:
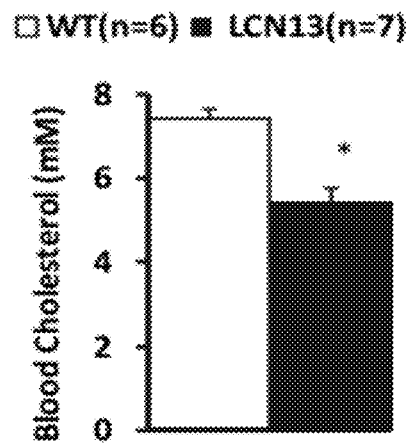
FIGS. 9A-9C illustrate experimental results indicating that LCN13 reduces blood cholesterol levels in obese mice and suppresses the lipogenic program. (A) LCN13 transgenic and control mice (7 wks) were fed a HFD for 15 weeks. Blood cholesterol levels were measured using commercial kits. (B) db/db mice were infected with β-gal (control) or LCN13 adenoviruses. Livers were isolated 15 days after infection, and liver triacylglycerol (TG) levels were measured, (C) db/db mice were infected with β-gal (control) or LCN13 adenoviruses. Livers were isolated 15 days after infection, and total RNAs were extracted. The expression of key lipogenic genes was measured by qRT-PCR.

LCN13 transgenic males and wild type littermates were fed a high fat diet (HFD) (45% fat). Blood samples were collected from tail vein and used to measure cholesterol levels. LCN13 significantly reduced blood cholesterol levels (FIG. 9A). These data demonstrate that LCN13 can be used to treat and prevent multiple cardiovascular diseases, including atherosclerosis, stroke, and heart attack.

LCN13 suppresses the lipogenic program and fatty liver diseases.

Figure 9B:
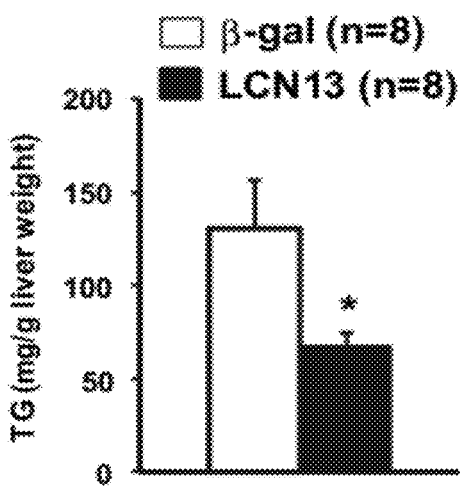
Figure 9C:
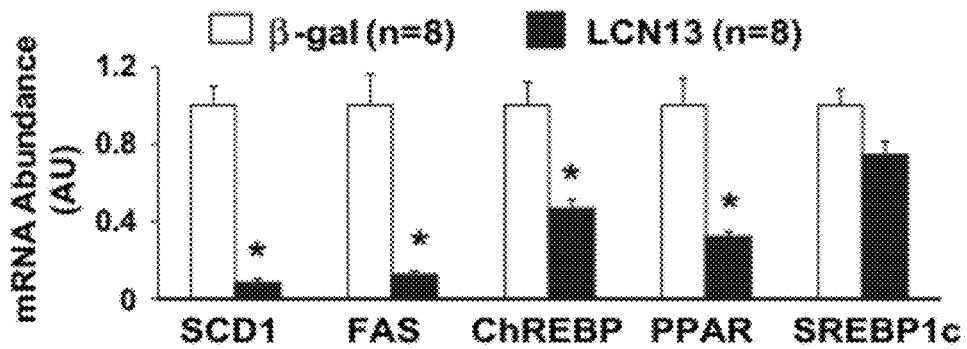

LCN13 was overexpressed in male mice with genetic obesity and type 2 diabetes (db/db) (lacking functional leptin receptor) via adenoviral infection. LCN13 markedly reduced liver lipid levels (FIG. 9B). LCN13 also dramatically suppressed the expression of many key genes that control hepatic lipogenic program (FIG. 9C). These results demonstrate that LCN13 can be used to treat various fatty liver diseases, such as alcoholic hepatitis, nonalcoholic fatty liver diseases (NAFLD) and nonalcoholic hepatitis (NASH).

Example 8

LCN13 Suppresses Lipogenesis in Primary Hepatocytes

Conditioned Medium

HepG2 cells were infected with β-gal or LCN13 adenoviruses, and culture medium was changed 24 hours after infection. Conditioned medium was collected 24 hours later.

Lipogenesis Assays

Primary hepatocyte cultures were prepared by liver-perfusion with type II collagenase (Worthington Biochem, Lakewood, N.J.) and grown on collagen-coated plates. Primary hepatocytes were pretreated with LCN13 recombinant protein, conditioned medium, or anti-LCN13 antibodies for 16 hours. The cells were then incubated for 4 hours in Williams Medium E (Sigma) supplemented with 0.5% BSA, 0.5 mM cold acetate, and 4 µCi/ml [$^3$H]-acetate (Moravek Biochemicals Inc, Brea, Calif.). Cells were lysed in 0.1 M HCl and lipids were extracted with chloroform/methanol (2:1). The organic phase was collected and dried by evaporation at 50° C. The pellets were dissolved in 50 µl hexane and 200 $H_2SO_4$ (1.8% in methanol) and heated for 30 min at 100° C. The mixtures were cooled down to room temperature, and mixed with 100 µl water and 250 µl petroleum. After centrifugation, petroleum phase was collected and used to measure [$^3$H] radioactivity. Lipogenesis rates were normalized to total protein levels.

Results

Figure 10A:
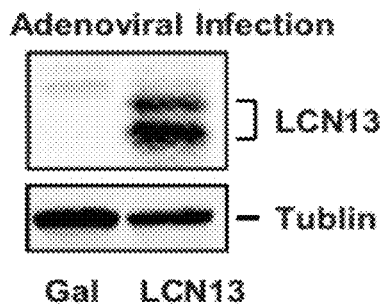
FIGS. 10A-10F illustrate experimental results indicating that LCN13 suppresses lipogenesis in primary hepatocytes. (A) Primary hepatocytes were infected with β-gal (Gal) or LCN13 (LCN) adenoviruses. Cell extracts were prepared 16 hours after viral infection and immunoblotted with anti-LCN13 antibody (αLCN13) or αtubulin. (B) Primary hepatocytes were infected with β-gal or LCN13 adenoviruses and subjected to lipogenesis assays 16 hours after infection. (C) HepG2 cells were infected with β-gal or LCN adenoviruses, and conditioned medium was collected 24 hours after viral infection. Conditioned medium (10 μl) was immunoblotted with αLCN13 (upper panel) or subjected to coomassie stains to visualize bovine serum albumin (low panel). (D) Primary hepatocytes were treated with conditioned medium for 16 hours and then subjected to lipogenesis assays. (E) Primary hepatocytes were treated with recombinant LCN13 proteins for 16 hours and then subjected to lipogenesis assays. (F) Primary hepatocytes were infected with β-gal or LCN13 adenoviruses. Total RNAs were extracted 16 hours after infection and used to measure the mRNA abundance of lipogenic genes by qRT-PCR. The expression of individual genes was normalized to 36B4 expression. Error bars represent SEM. *P<0.05.
Figure 10B:
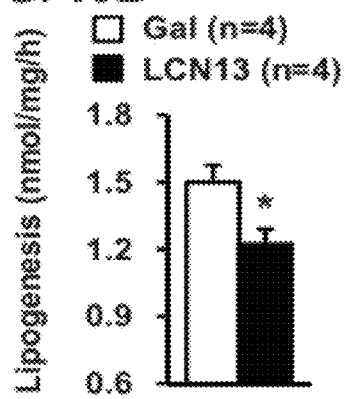

To overexpress LCN13, primary hepatocytes were prepared from C57BL/6 male mice (8-9 weeks) and infected with LCN13 or β-gal adenoviruses as described previously. LCN13 was detected in LCN13-, but not β-gal-adenovirus-infected cells (FIG. 10A). Two forms of LCN13 were detected that likely resulted from differential proteolysis of a common LCN13 precursor. Hepatocytes were subjected to lipogenesis assays 16 hours after infection. LCN13 overexpression reduced lipogenesis by 18% (FIG. 10B).

Figure 10C:
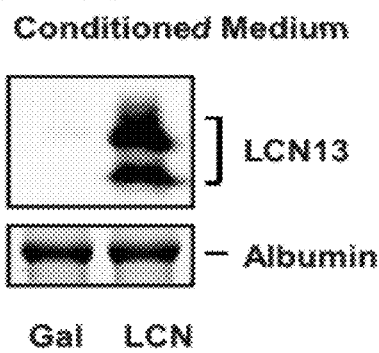
Figure 10D:
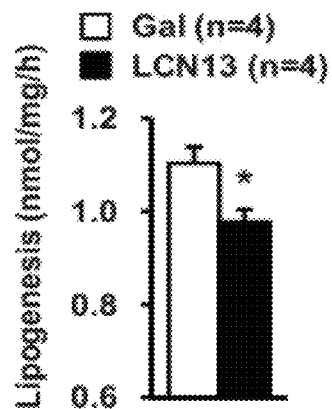
Figure 10E:
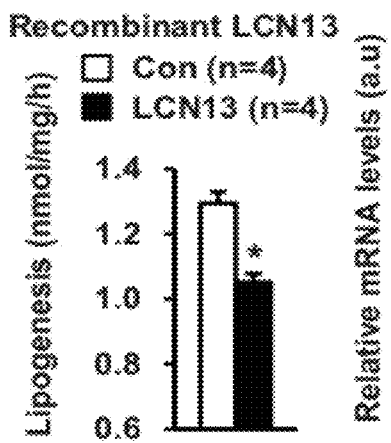

To verify these findings by a different approach, LCN13 conditioned medium was prepared from HepG2 cells (human hepatoblastoma cells). HepG2 cells were infected with LCN13 or β-gal adenoviruses, and LCN13 or β-gal conditioned medium was collected as described above. Recombinant LCN13 proteins were detected in LCN13 conditioned medium but not β-gal conditioned medium (FIG. 10C). Primary hepatocytes were treated with LCN13 or β-gal conditioned medium for 16 hours and then subjected to lipogenesis assays. LCN13 conditioned medium inhibited lipogenesis by >11% (FIG. 10D). To further analyze LCN13 action, recombinant LCN13 was produced and purified from bacteria. Primary hepatocytes were treated with recombinant LCN13 for 16 hours and subjected to lipogenesis assays. Recombinant LCN13 inhibited lipogenesis by 19% (FIG. 10E). Together, these results demonstrate that LCN13 is a novel negative regulator of hepatic lipogenesis.

Figure 10F:
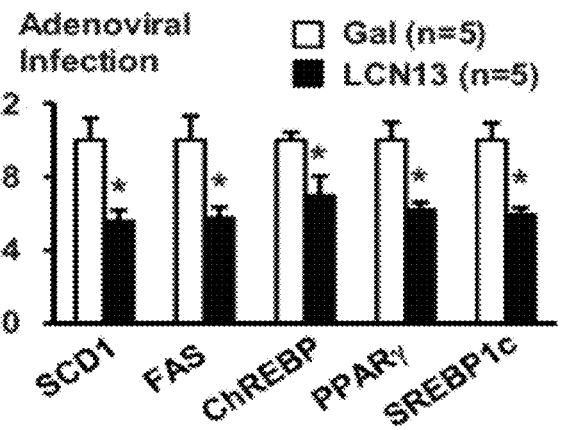

Hepatic lipogenesis rates are controlled by key transcription factors and metabolic enzymes, including peroxisome proliferator-activated receptor (PPAR)$_y$, sterol regulatory element binding protein (SREBP)1c, carbohydrate responsive element-binding protein (ChREBP), stearoyl-Coenzyme A desaturase 1 (SCD1), and fatty acid synthase (FAS). To determine whether LCN13 inhibits the expression of these lipogenic genes, the mRNA abundance of these genes was measured. Primary hepatocytes were infected with LCN13 or β-gal adenoviruses, and total RNAs were extracted 16 hours after infection and used to measure the mRNA abundance of these lipogenic regulators by qRT-PCR. LCN13 overexpression significantly inhibited the expression of SCD1, FAS, ChREBP, PPARy, and SREBP1c (FIG. 10F). These data suggest that LCN13 directly inhibits the hepatic lipogenic program.

Example 9

LCN13 Stimulates Fatty Acid β Oxidation in Primary Hepatocytes

Fatty Acid β Oxidation Assays

Primary hepatocytes were treated as described above. The treated cells were incubated for 1 hour at 37° C. with 0.4 µCi/ml [9,10-$^3$H(N)]-oleic acid (Moravek Biochemicals Inc, Brea, Calif.) 100 µM cold oleic acid (conjugated with BSA) in Krebs-Ringer buffer (119 mM NaCl, 5 mM KCl, 2 mM $CaCl_2$, 2.6 mM $MgSO_4$, 24.6 mM $NaHCO_3$, 2.6 mM $KH_2PO_4$, 10 mM HEPES, pH 7.4). Supernatant was collected, incubated with perchloric acid (1.3 M), and centrifuged at 16,000 rcf for 10 min.

Results

Figure 11A:
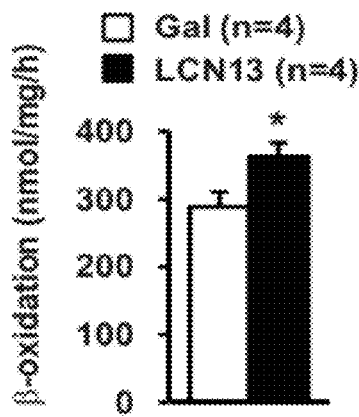
FIGS. 11A-11D illustrate experimental results indicating that LCN13 promotes fatty acid β oxidation in primary hepatocytes. (A) Primary hepatocytes were infected with β-gal or LCN13 adenoviruses, and fatty acid β oxidation rates were measured 16 hours after viral infection. (B) Primary hepatocytes were treated with conditioned medium for 16 hours and then subjected to β oxidation. (C) Primary hepatocytes were treated with recombinant LCN13 proteins for 16 hours and then subjected to β oxidation assays. (D) Primary hepatocytes were with β-gal or LCN13 adenoviruses. Total RNAs were extracted 16 hours after infection and used to measure mRNA abundance of the indicated genes by qRT-PCR. The expression of individual genes was normalized to 36B4 expression. Error bars represent SEM. *P<0.05.
Figure 11B:
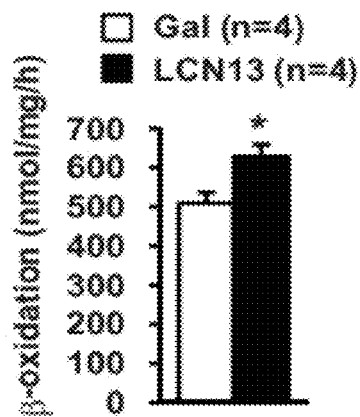
Figure 11C:
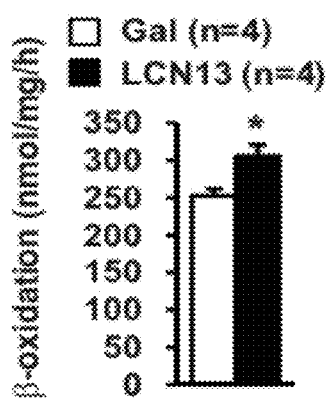
Figure 11D:
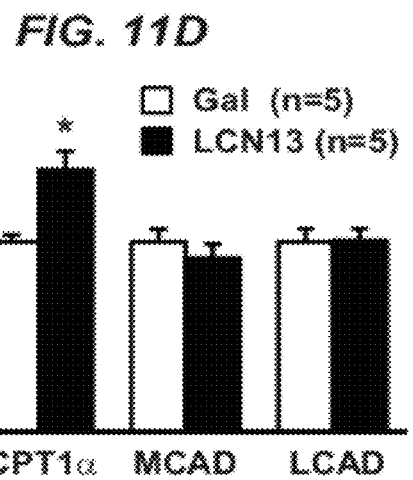

Primary hepatocytes were infected with LCN13 or β-gal adenoviruses as described in FIG. 10A and subjected to β oxidation assays 16 hours after infection. LCN13 overexpression increased fatty acid β oxidation rates by 26% (FIG. 11A). To confirm these findings by an independent approach, primary hepatocytes were treated with LCN13 or β-gal conditioned medium for 16 hours and subjected to β oxidation assays. LCN13 conditioned medium treatments increased β oxidation rates by 23% (FIG. 11B). To further examine LCN13 action, primary hepatocyte cultures were treated with purified, bacteria-derived recombinant LCN13. Recombinant LCN13 also stimulated β oxidation rates by 21% (FIG. 11C). The effect of LCN13 on the expression of carnitine palmitoyltransferase (CPT) Iα (liver form), long chain acyl coA dehydrogenase (LCAD), and medium chain acyl coA dehydrogenase (MCAD) that mediate β oxidation was also examined. Primary hepatocytes were infected with LCN13 or β-gal adenoviruses, and total RNAs were extracted 16 hours after infection and used to measure the mRNA abundance of CPT1α, MCAD and LCAD by qRT-PCR. LCN13 overexpression significantly increased the expression of CPT1α but not MCAD and LCAD (FIG. 11D). Therefore, LCN13 directly stimulates fatty acid β oxidation in hepatocytes, at least in part by stimulating CPT1α expression.

Example 10

Chronic Overexpression of LCN13 Protects Against Hepatosteatosis in Mice with Diet-Induced Obesity To determine whether LCN13 regulates hepatic lipid metabolism in animals, we performed studies in LCN13 transgenic (Tg) mice. In Tg mice, the expression of the LCN13 transgene is under the control of the constitutively active chicken β-actin/rabbit β-globin hybrid promoter. To determine whether chronic LCN13 overexpression protects against diet-induced hepatic steatosis, Tg and control male littermates (7 weeks) were fed a high fat diet (HFD). Body weight was similar between Tg and WT mice at 18 weeks of age (Tg: 39.5±1.4 g, n=9; WT: 41.6±1.5 g, n=10; p=0.38). Plasma triacylglycerol (TAG) levels decreased by 12% in Tg mice at 18 weeks of age (FIG. 12A). Liver weights were similar between WT and Tg mice (FIG. 12B); however, liver TAG contents decreased by 40% in Tg mice at 20 weeks of age (FIG. 12C). In agreement with the findings in primary hepatocytes, chronic LCN13 overexpression significantly inhibited the expression of key lipogenic genes (e.g., SCD1, FAS, ChREBP, PPARγ, and SREBP1c) but stimulated CPT1α expression in the liver (FIG. 12D). These results indicate that LCN13 suppresses lipogenesis and enhances fatty acid β oxidation in the liver.

Example 11

LCN13 Protects Against Hepatosteatosis in Mice with Genetic Obesity

Figure 13A:
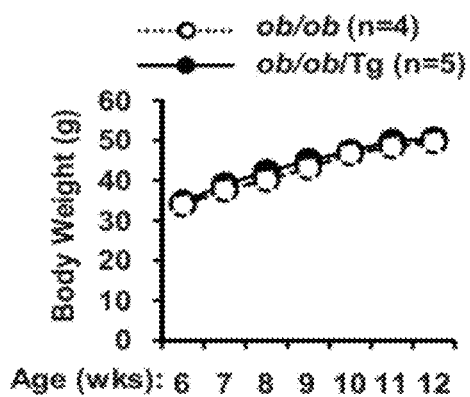
FIGS. 13A-13D illustrate experimental results indicating that transgenic overexpression of LCN13 improves insulin resistance, hyperglycemia and glucose intolerance in ob/ob mice. ob/ob and ob/ob/Tg males were fed normal chow. (A) Growth curves. (B) Fasting (16 hours) and randomly-fed blood glucose levels at 10 weeks of age. (C) GTT: Mice (10 weeks) were fasted overnight and intraperitoneally injected with D-glucose (0.5 g/kg body weight). Blood glucose levels were monitored. (D) ITT: Mice (10 weeks) were fasted for 6 hours and intraperitoneally injected with human insulin (2.5 unites/kg body weight). Blood glucose levels were monitored. Error bars represent SEM. *P<0.05.
Figure 13B:
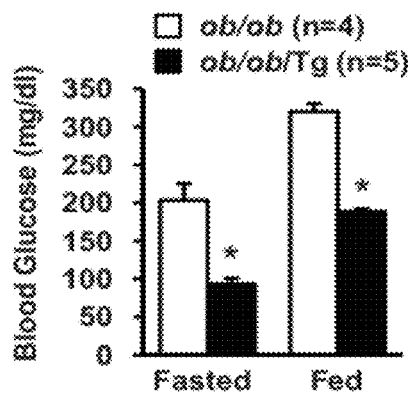
Figure 13C:
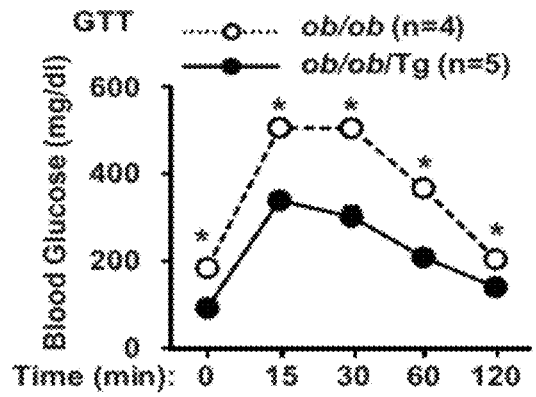
Figure 13D:
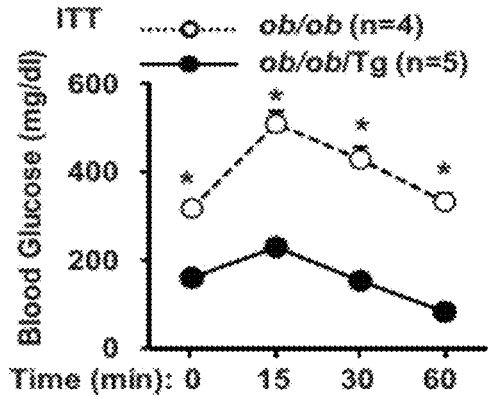

To determine whether overexpression of LCN13 similarly protects against hepatosteatosis in mice with genetic obesity, Tg mice were crossed with $ob^{+/-}$ mice to generate LCN13 transgenic and leptin-deficient double mutant mice (ob/ob/Tg). ob/ob mice have been commonly used as a genetic model of obesity. LCN13 overexpression did not alter body weights of ob/ob/Tg mice (FIG. 13A). However, transgenic overexpression of LCN13 markedly reduced both fasted (by 54%) and randomly-fed blood glucose (by 41%) in ob/ob/Tg mice (FIG. 13B). To further analyze glucose metabolism, we performed glucose tolerance tests (GTT) and insulin tolerance tests (ITT). In GTT, blood glucose levels were significantly lower in ob/ob/Tg than in ob/ob mice at each time point after glucose injection (FIG. 13C). In ITT, insulin was unable to reduce blood glucose in ob/ob mice due to insulin resistance; however, chronic LCN13 overexpression increased the ability of insulin to reduce blood glucose in ob/ob/Tg mice (FIG. 13D). These results are consistent with the results presented in Example 2 that LCN13 improves glucose metabolism in part by sensitizing insulin action.

Plasma TAG levels decreased by 18% in ob/ob/Tg mice compared with ob/ob mice (FIG. 14A). Liver weights decreased in ob/ob/Tg mice (13 weeks), but the difference between ob/ob and ob/ob/Tg mice was not statistically significant (FIG. 14B). Liver structures were examined by hematoxylin & eosin (H & E) staining and measuring hepatic lipid levels using biochemical assays. The sizes of lipid droplets and the number of large lipid droplets were markedly decreased in ob/ob/Tg mice (FIG. 14C). In agreement, liver TAG contents were significantly lower in ob/ob/Tg than in ob/ob mice (FIG. 14D). Furthermore, the expression of lipogenic genes (e.g. SCD1, FAS, ChREBP, PPARγ and SREBP1c) was significantly reduced in ob/ob/Tg mice, whereas CPT1α expression increased in LCN13-overexpressing mice with genetic obesity (FIG. 14E). These data indicate that LCN13 is able to suppress hepatic lipogenesis, promote β oxidation, and ameliorate hepatosteatosis and NAFLD in obesity.

Figure 15A:
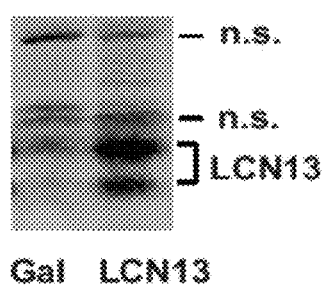
FIGS. 15A-15C illustrate experimental results indicating that liver-specific overexpression of LCN13 attenuates hepatosteatosis in db/db mice. db/db males (9 weeks) were infected with β-gal or LCN13 adenoviruses via tail vein injection, and the mice were euthanized 16 days after viral infection. (A) Liver extracts were immunoblotted with αLCN13. n.s.: non-specific bands. (B) Liver weights. (C) Liver TAG levels (normalized to liver weights). Error bars represent SEM. *P<0.05.
Figure 15B:
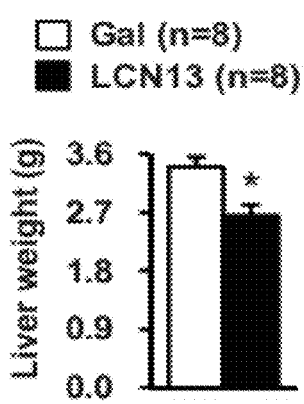
Figure 15C:
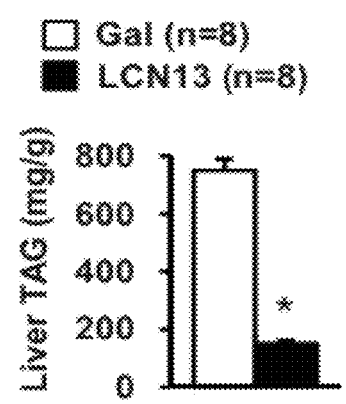

To determine whether a short-term LCN13 treatment improves hepatosteatosis in obesity, db/db mice (9 weeks) were infected with LCN13 or β-gal adenoviruses via tail vein injection, and livers were harvested 16 days after infection. db/db mice are deficient of functional leptin receptors and widely used as a genetic model of obesity. Recombinant LCN13 was detected as two forms in LCN13 adenovirus-infected livers (FIG. 15A). Liver weights decreased in LCN13-overexpressing mice (FIG. 15B). Liver TAG contents decreased by 80% in LCN13 adenovirus-infected mice compared with that in β-gal adenovirus-infected mice (FIG. 6C). Taken together, these data indicate that LCN13 therapy attenuates hepatosteatosis at least in part by suppressing hepatic lipogenesis and/or promoting 13 oxidation in the liver.

Example 12

Figure 16A:
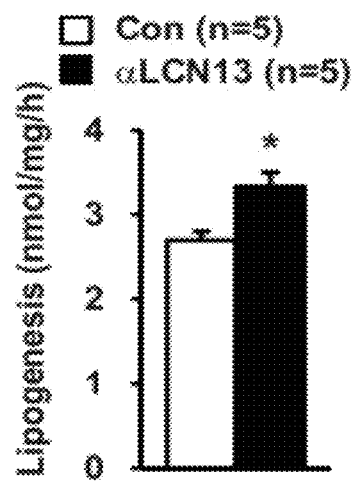
FIGS. 16A-16C illustrate experimental results indicating that endogenous LCN13 regulates hepatic lipogenesis and β oxidation in an autocrine/paracrine fashion. Primary hepatocytes were treated with αLCN13 or pre-immune serum (Con). Lipogenesis rates (A) and fatty acid β oxidation rates (B) were measured 16 hours after the treatments. (C) Total RNAs were extracted 16 hours after the treatments and used to measure the expression of the indicated genes (normalized to 36B4 expression). Error bars represent SEM. *P<0.05.
Figure 16B:
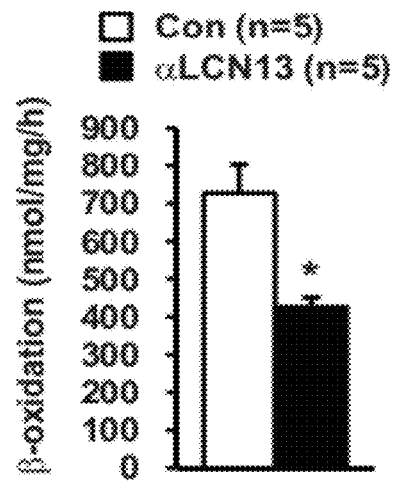
Figure 16C:
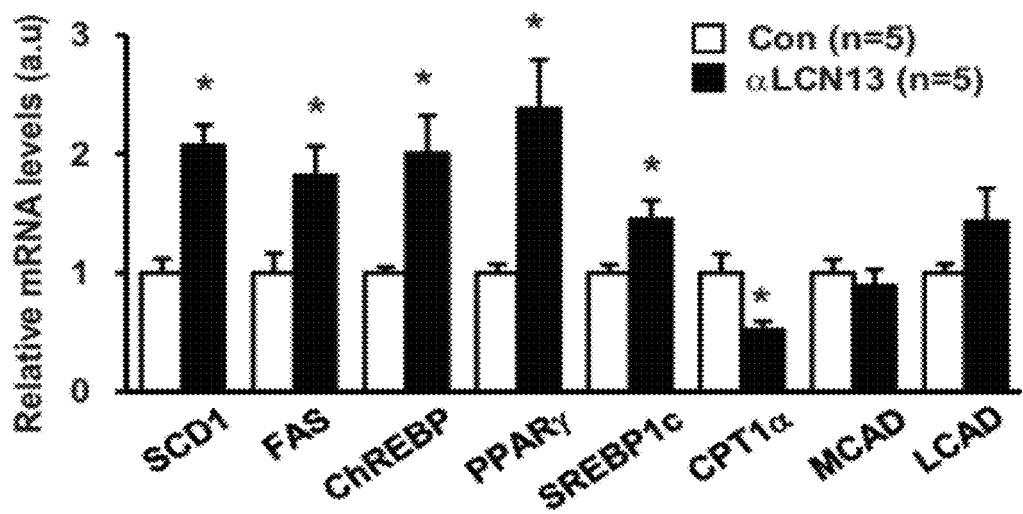

Endogenous LCN13 Regulates Hepatic Lipid Metabolism in an Autocrine/Paracrine Fashion To determine whether endogenous LCN13 regulates lipogenesis and β oxidation, primary hepatocytes were treated with anti-LCN13 antibody to neutralize hepatocyte-secreted LCN13 in culture medium. Pre-immune serum was used as control. The treated cells were then subjected to lipogenesis or β oxidation assays. Neutralization of endogenous LCN13 increased lipogenesis by 24% (FIG. 16A) and decreased fatty acid β oxidation by 41% (FIG. 16B). The expression of genes that control lipogenesis and β oxidation by qRT-PCR was also examined. In contrast to LCN13 treatments, neutralization of LCN13 significantly increased the expression of lipogenic genes (e.g., SCD1, FAS, ChREBP, PPARγ, and SREBP1c) and decreased CPT1α expression (FIG. 16C). These data indicate that endogenous LCN13 in the liver regulates hepatic lipogenesis and β oxidation in an autocrine/paracrine manner.

What is claimed:

1. A method of treating a lipocalin (LCN)13-related condition comprising administering to a patient in need thereof a therapeutically effective amount of a lipocalin selected from the group consisting of LCN13, LCN1, LCN3, LCN4, LCN14, odorant binding protein (OBP)2B, OBP2A, and a fragment of LCN13 comprising residues 54 through 124 in SEQ ID NO: 1, wherein the LCN-13 related condition is a metabolic disorder or a cardiovascular disease.

2. The method of claim 1 wherein said lipocalin is at least 95% identical to SEQ ID NO: 1.

3. The method of claim 1 wherein said lipocalin comprises the amino acid sequence set out in SEQ ID NO: 1.

4. The method of claim 1 wherein said metabolic disorder is selected from the group consisting of type 1 diabetes, type 2 diabetes, hyperglycemia, hyperinsulinemia, insulin resistance, and obesity.

5. The method of claim 4 wherein said lipocalin is co-administered with a therapeutically effective amount of insulin.

6. The method of claim 1 wherein the cardiovascular disease is selected from the group consisting of hypercholesterolemia, non-familial hypercholesterolemia, familial hypercholesterolemia, heterozygous familial hypercholesterolemia, homozygous familial hypercholesterolemia, mixed dyslipidemia, atherosclerosis, coronary heart disease, early onset coronary heart disease, dyslipidemia, hypertriglyceridemia, hyperlipidemia, and hyperfattyacidemia.

7. The method of claim 1, wherein the LCN-13 related condition is a cardiovascular disease selected from the group consisting of hepatic steatosis, non-alcoholic steatohepatitis, cirrhosis, liver failure, and non-alcoholic fatty liver disease.

* * * * *

SEQUENCE LISTING

<160> NUMBER OF SEQ ID NOS: 35

<210> SEQ ID NO 1
<211> LENGTH: 176
<212> TYPE: PRT
<213> ORGANISM: Mus musculus

<400> SEQUENCE: 1

Met Lys Ser Leu Leu Leu Thr Ile Leu Leu Gly Leu Val Ala Val
1               5                   10                  15

Leu Lys Ala Gln Glu Ala Pro Pro Asp Asp Leu Val Asp Tyr Ser Gly
            20                  25                  30

Ile Trp Tyr Ala Lys Ala Met Val His Asn Gly Thr Leu Pro Ser His
        35                  40                  45

Lys Ile Pro Ser Ile Val Phe Pro Val Arg Ile Ile Ala Leu Glu Glu
    50                  55                  60

Gly Asp Leu Glu Thr Thr Val Val Phe Trp Asn Asn Gly His Cys Arg
65                  70                  75                  80

Glu Phe Lys Phe Val Met Lys Lys Thr Glu Glu Pro Gly Lys Tyr Thr
                85                  90                  95

Ala Phe His Asn Thr Lys Val Ile His Val Glu Lys Thr Ser Val Asn
                100                 105                 110

Glu His Tyr Ile Phe Tyr Cys Glu Gly Arg His Asn Gly Thr Ser Ser
            115                 120                 125

Phe Gly Met Gly Lys Leu Met Gly Arg Asp Ser Gly Glu Asn Pro Glu
        130                 135                 140

Ala Met Glu Glu Phe Lys Asn Phe Ile Lys Arg Met Asn Leu Arg Leu
145                 150                 155                 160

Glu Asn Met Phe Val Pro Glu Ile Gly Asp Lys Cys Val Glu Ser Asp
                165                 170                 175

<210> SEQ ID NO 2
<211> LENGTH: 19
<212> TYPE: DNA
<213> ORGANISM: Artificial Sequence
<220> FEATURE:
<223> OTHER INFORMATION: Synthetic primer

<400> SEQUENCE: 2
gtcattcggg atgggaaag                                                19

<210> SEQ ID NO 3
<211> LENGTH: 19
<212> TYPE: DNA
<213> ORGANISM: Artificial Sequence
<220> FEATURE:
<223> OTHER INFORMATION: Synthetic primer

<400> SEQUENCE: 3
gctgttgcag acctgggta                                                19

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
aaatcgtgcg tgacatcaaa                                               20

```
<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
aaggaaggct ggaaaagagc                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
atcatctttg gtggccgtag                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
atcttgccct tgtgttctgc                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
ccggtgtttg aacgtcatct                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
caatgcctga caagactcca                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
tggacggaag caatttttca                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 11
ttacctgcgc aagcttctct                                              20

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
aagcgcgtcc tggcattgtc t                                            21

<210> SEQ ID NO 13
<211> LENGTH: 19
<212> TYPE: DNA
<213> ORGANISM: Artificial Sequence
<220> FEATURE:
<223> OTHER INFORMATION: Synthetic primer

<400> SEQUENCE: 13
ccgcaggggc agcagtggt                                               19

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
ctggggacct aaacaggagc                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
gaagccaccc tatagctccc                                              20

<210> SEQ ID NO 16
<211> LENGTH: 21
<212> TYPE: DNA
<213> ORGANISM: Artificial Sequence
<220> FEATURE:
<223> OTHER INFORMATION: Synthetic primer

<400> SEQUENCE: 16
ctgatgacgg ctatggtgtt t                                            21

<210> SEQ ID NO 17
<211> LENGTH: 21
<212> TYPE: DNA
<213> ORGANISM: Artificial Sequence
<220> FEATURE:
<223> OTHER INFORMATION: Synthetic primer

<400> SEQUENCE: 17
gtgaggccaa acaaggtgat a                                            21

<210> SEQ ID NO 18
<211> LENGTH: 20
```

```
<212> TYPE: DNA
<213> ORGANISM: Artificial Sequence
<220> FEATURE:
<223> OTHER INFORMATION: Synthetic primer

<400> SEQUENCE: 18
ttgacggctc acacacctac                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
cgatcttcca ggctcttcag                                               20

<210> SEQ ID NO 20
<211> LENGTH: 22
<212> TYPE: DNA
<213> ORGANISM: Artificial Sequence
<220> FEATURE:
<223> OTHER INFORMATION: Synthetic primer

<400> SEQUENCE: 20
cactcagata ttgtcatgcc ct                                            22

<210> SEQ ID NO 21
<211> LENGTH: 22
<212> TYPE: DNA
<213> ORGANISM: Artificial Sequence
<220> FEATURE:
<223> OTHER INFORMATION: Synthetic primer

<400> SEQUENCE: 21
tccattgaga atccaatcac tc                                            22

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
accctgtgga gaagctgatg                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
agcaacagtg cttggagctt                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
ccagagtctg ctgatctgcg                                               20
```

-continued

<210> SEQ ID NO 25
<211> LENGTH: 20
<212> TYPE: DNA
<213> ORGANISM: Artificial Sequence
<220> FEATURE:
<223> OTHER INFORMATION: Synthetic primer

<400> SEQUENCE: 25
gccacctctt tgctctgatc                                                   20

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
aggtgcctct tagccactga                                                   20

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
ccaggagttt cttgggttga                                                   20

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
aacgtcactt ccagctagac                                                   20

<210> SEQ ID NO 29
<211> LENGTH: 21
<212> TYPE: DNA
<213> ORGANISM: Artificial Sequence
<220> FEATURE:
<223> OTHER INFORMATION: Synthetic primer

<400> SEQUENCE: 29
ccactaaggt gcctacagag c                                                 21

<210> SEQ ID NO 30
<211> LENGTH: 176
<212> TYPE: PRT
<213> ORGANISM: Homo sapiens

<400> SEQUENCE: 30

Met Lys Pro Leu Leu Leu Ala Val Ser Leu Gly Leu Ile Ala Ala Leu
1               5                   10                  15

Gln Ala His His Leu Leu Ala Ser Asp Glu Glu Ile Gln Asp Val Ser
            20                  25                  30

Gly Thr Trp Tyr Leu Lys Ala Met Thr Val Asp Arg Glu Phe Pro Glu
        35                  40                  45

Met Asn Leu Glu Ser Val Thr Pro Met Thr Leu Thr Thr Leu Glu Gly
    50                  55                  60

```
Gly Asn Leu Glu Ala Lys Val Thr Met Leu Ile Ser Gly Arg Cys Gln
 65                  70                  75                  80

Glu Val Lys Ala Val Leu Glu Lys Thr Asp Glu Pro Gly Lys Tyr Thr
                 85                  90                  95

Ala Asp Gly Gly Lys His Val Ala Tyr Ile Ile Arg Ser His Val Lys
            100                 105                 110

Asp His Tyr Ile Phe Tyr Cys Glu Gly Glu Leu His Gly Lys Pro Val
        115                 120                 125

Arg Gly Val Lys Leu Val Gly Arg Asp Pro Lys Asn Asn Leu Glu Ala
    130                 135                 140

Leu Glu Asp Phe Glu Lys Ala Ala Gly Ala Arg Gly Leu Ser Thr Glu
145                 150                 155                 160

Ser Ile Leu Ile Pro Arg Gln Ser Glu Thr Cys Ser Pro Gly Ser Asp
                165                 170                 175
```

<210> SEQ ID NO 31
<211> LENGTH: 187
<212> TYPE: PRT
<213> ORGANISM: Mus musculus

<400> SEQUENCE: 31

```
Met Gln Thr Leu Glu Met Arg Ala Leu Leu Leu Ile Ile Ser Phe Cys
 1               5                  10                  15

Leu Val Ala Val Leu Gln Ala Gln Asp Ser Ser Phe Leu Ala Phe Asn
                20                  25                  30

Asn Gly Asn Phe Ser Gly Lys Trp Phe Leu Lys Ala Leu Val Ser Glu
            35                  40                  45

Asp Asp Ile Pro Ile Asn Lys Val Ser Pro Met Leu Ile Leu Val Leu
        50                  55                  60

Asn Asn Gly Asp Ile Glu Leu Ser Ile Thr His Met Ile Tyr Asp Gln
 65                  70                  75                  80

Cys Leu Glu Val Thr Thr Ile Leu Glu Lys Thr Asp Val Pro Gly Gln
                 85                  90                  95

Tyr Leu Ala Phe Glu Gly Lys Thr His Leu Gln Val Gln Leu Ser Ser
            100                 105                 110

Val Lys Gly His Tyr Met Leu Tyr Cys Asp Gly Glu Ile Glu Gly Met
        115                 120                 125

Arg Phe Leu Met Thr Gln Leu Ile Gly Arg Asp Pro Gln Glu Asn Leu
    130                 135                 140

Glu Ala Leu Glu Glu Phe Lys Val Phe Thr Gln Ile Lys Gly Leu Val
145                 150                 155                 160

Ala Glu Asn Leu Val Ile Leu Glu Gln Met Glu Lys Cys Glu Pro Glu
                165                 170                 175

Ser Phe Tyr Glu Leu Pro Ser Arg Pro Ser Glu
            180                 185
```

<210> SEQ ID NO 32
<211> LENGTH: 185
<212> TYPE: PRT
<213> ORGANISM: Mus musculus

<400> SEQUENCE: 32

```
Met Lys Ser Leu Leu Leu Thr Val Thr Leu Ser Ser Leu Val Ala Thr
 1               5                  10                  15

Leu Gln Thr Tyr Asp Asp Leu Pro Phe Ile Ser Glu Glu Asp Lys Leu
                20                  25                  30
```

```
Ser Gly Val Trp Phe Ile Lys Ala Thr Val Ser Gln Arg Arg Glu Val
            35                  40                  45

Glu Gly Glu Thr Leu Val Ala Phe Pro Ile Lys Phe Thr Cys Pro Glu
 50                  55                  60

Glu Gly Thr Leu Glu Leu Arg His Thr Leu Ala Ser Lys Gly Glu Cys
 65                  70                  75                  80

Ile Asn Val Gly Ile Arg Leu Gln Arg Thr Glu Glu Pro Gly Gln Tyr
                 85                  90                  95

Ser Ala Phe Trp Gly His Thr Leu Phe Tyr Ile Tyr Asp Leu Pro Val
            100                 105                 110

Lys Asp His Tyr Ile Ile Tyr Cys Glu Ser His Pro Phe Gln Lys Ile
            115                 120                 125

Ser Gln Phe Gly Tyr Leu Ile Gly Lys Tyr Pro Glu Glu Asn Gln Asp
            130                 135                 140

Thr Leu Glu Val Phe Lys Glu Phe Ile Gln His Lys Gly Phe Leu Gln
145                 150                 155                 160

Glu Lys Ile Gly Val Pro Glu Gln Arg Asp Arg Cys Ile Pro Ile His
                165                 170                 175

Asp Ser Ala His Gln Asp His Lys Cys
                180                 185

<210> SEQ ID NO 33
<211> LENGTH: 176
<212> TYPE: PRT
<213> ORGANISM: Mus musculus

<400> SEQUENCE: 33

Met Lys Ser Leu Leu Leu Thr Ile Leu Leu Gly Leu Val Ala Val
 1               5                  10                  15

Leu Lys Ala Gln Glu Ala Pro Pro Asp Asp Leu Glu Asp Phe Ser Gly
            20                  25                  30

Ile Trp Tyr Thr Gln Ala Met Val Ser Asp Arg Asn His Thr Asp Gly
            35                  40                  45

Lys Arg Pro Met Lys Val Phe Pro Met Thr Val Ile Ala Leu Glu Gly
 50                  55                  60

Gly Ser Leu Glu Ala Gln Leu Thr Phe Trp Asp Asn Gly His Cys His
 65                  70                  75                  80

Met Lys Lys Ile Leu Met His Lys Thr Asp Glu Pro His Lys Tyr Thr
                 85                  90                  95

Ala Phe Lys Gly Lys Lys Thr Ile Tyr Ile Gln Glu Thr Ser Val Lys
            100                 105                 110

Gly Tyr Tyr Ile Leu Tyr Cys Glu Gly Gln Arg His Gly Arg Ser His
            115                 120                 125

Arg Lys Gly Lys Leu Ile Gly Thr Asn Ser Glu Lys Asn Pro Glu Ala
            130                 135                 140

Met Glu Glu Phe Lys Lys Phe Ala Met Ser Lys Gly Phe Arg Glu Glu
145                 150                 155                 160

Asn Ile Ile Val Pro Glu Gln Leu Asp Gln Cys Val Ser Gly Ser Asn
                165                 170                 175

<210> SEQ ID NO 34
<211> LENGTH: 170
<212> TYPE: PRT
<213> ORGANISM: Homo sapiens

<400> SEQUENCE: 34

Met Lys Thr Leu Phe Leu Gly Val Thr Leu Gly Leu Ala Ala Ala Leu
```

```
  1               5                  10                 15
Ser Phe Thr Leu Glu Glu Glu Asp Ile Thr Gly Thr Trp Tyr Val Lys
             20                 25                 30

Ala Met Val Val Asp Lys Asp Phe Pro Glu Asp Arg Arg Pro Arg Lys
             35                 40                 45

Val Ser Pro Val Lys Val Thr Ala Leu Gly Gly Gly Lys Leu Glu Ala
             50                 55                 60

Thr Phe Thr Phe Met Arg Glu Asp Arg Cys Ile Gln Lys Lys Ile Leu
 65              70                 75                 80

Met Arg Lys Thr Glu Glu Pro Gly Lys Tyr Ser Ala Tyr Gly Gly Arg
             85                 90                 95

Lys Leu Met Tyr Leu Gln Glu Leu Pro Arg Arg Asp His Tyr Ile Phe
             100                105                110

Tyr Cys Lys Asp Gln His His Gly Leu Leu His Met Gly Lys Leu
             115                120                125

Val Gly Arg Asn Ser Asp Thr Asn Arg Glu Ala Leu Glu Glu Phe Lys
             130                135                140

Lys Leu Val Gln Arg Lys Gly Leu Ser Glu Glu Asp Ile Phe Thr Pro
145              150                155                160

Leu Gln Thr Gly Ser Cys Val Pro Glu His
             165                170

<210> SEQ ID NO 35
<211> LENGTH: 170
<212> TYPE: PRT
<213> ORGANISM: Homo sapiens

<400> SEQUENCE: 35

Met Lys Thr Leu Phe Leu Gly Val Thr Leu Gly Leu Ala Ala Ala Leu
 1               5                  10                 15

Ser Phe Thr Leu Glu Glu Glu Asp Ile Thr Gly Thr Trp Tyr Val Lys
             20                 25                 30

Ala Met Val Val Asp Lys Asp Phe Pro Glu Asp Arg Arg Pro Arg Lys
             35                 40                 45

Val Ser Pro Val Lys Val Thr Ala Leu Gly Gly Gly Asn Leu Glu Ala
             50                 55                 60

Thr Phe Thr Phe Met Arg Glu Asp Arg Cys Ile Gln Lys Lys Ile Leu
 65              70                 75                 80

Met Arg Lys Thr Glu Glu Pro Gly Lys Phe Ser Ala Tyr Gly Gly Arg
             85                 90                 95

Lys Leu Ile Tyr Leu Gln Glu Leu Pro Gly Thr Asp Asp Tyr Val Phe
             100                105                110

Tyr Cys Lys Asp Gln Arg Arg Gly Gly Leu Arg Tyr Met Gly Lys Leu
             115                120                125

Val Gly Arg Asn Pro Asn Thr Asn Leu Glu Ala Leu Glu Glu Phe Lys
             130                135                140

Lys Leu Val Gln His Lys Gly Leu Ser Glu Glu Asp Ile Phe Met Pro
145              150                155                160

Leu Gln Thr Gly Ser Cys Val Leu Glu His
             165                170
```